(12) United States Patent
Rudy et al.

(10) Patent No.: US 6,975,900 B2
(45) Date of Patent: Dec. 13, 2005

(54) SYSTEMS AND METHODS FOR DETERMINING A SURFACE GEOMETRY

(75) Inventors: Yoram Rudy, Shaker Heights, OH (US); Charulatha Ramanathan, Richmond Heights, OH (US); Raja Ghanem, Cleveland Heights, OH (US); Ping Jia, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 268 days.

(21) Appl. No.: 10/317,953

(22) Filed: Dec. 12, 2002

(65) Prior Publication Data

US 2004/0082870 A1 Apr. 29, 2004

Related U.S. Application Data

(63) Continuation-in-part of application No. 10/264,572, filed on Oct. 4, 2002, which is a continuation-in-part of application No. 10/037,603, filed on Oct. 19, 2001, now Pat. No. 6,772,004, which is a continuation of application No. 09/463,428, filed as application No. PCT/US98/15927 on Jul. 29, 1998, now abandoned.
(60) Provisional application No. 60/327,419, filed on Oct. 4, 2001, and provisional application No. 60/054,342, filed on Jul. 31, 1997.

(51) Int. Cl.⁷ .............................................. A61B 5/044
(52) U.S. Cl. ........................ 600/523; 128/920; 600/411
(58) Field of Search ................................. 600/509, 523, 600/407, 411, 513, 427; 128/920

(56) References Cited

U.S. PATENT DOCUMENTS

| | | |
|---|---|---|
| 3,848,582 A | 11/1974 | Milani et al. |
| 3,858,576 A | 1/1975 | Dehnert et al. |
| 4,033,336 A | 7/1977 | Murawski et al. |
| 4,183,354 A | 1/1980 | Sibley et al. |
| 4,203,451 A | 5/1980 | Panico |
| 4,535,783 A | 8/1985 | Marangoni |
| 4,593,698 A | 6/1986 | Athans |

(Continued)

OTHER PUBLICATIONS

Jia, Ping et al., Electrophysiologic Endocardial Mapping from a Noncontact Nonexpandable Catheter: A Validation Study of a Geometry–Based Concept, J Cardiovasc Electrophysiol, vol. 11, pp. 1238–1251, Nov. 2000.

(Continued)

*Primary Examiner*—Kennedy Schaetzle
(74) *Attorney, Agent, or Firm*—Foley Hoag LLP; Scott E. Kamholz

(57) ABSTRACT

Methods and systems for determining a surface geometry of an object, including determining a first projection matrix based on a first imaging device, determining a second projection matrix based on a second imaging device, obtaining at least one first two-dimensional (2D) image of the object using the first imaging device, obtaining at least one second 2D image of the object using the second imaging device, determining a contour of the object in the first 2D image and the second 2D image, and, based on the at least two contours, the first projection matrix, and the second projection matrix, reconstructing 3D data associated with the surface of the object. In one embodiment, the object can be a heart.

8 Claims, 25 Drawing Sheets

U.S. PATENT DOCUMENTS

| | | | |
|---|---|---|---|
| 4,606,352 A | 8/1986 | Geddes et al. | |
| 4,649,924 A | 3/1987 | Taccardi | 128/642 |
| 4,805,631 A | 2/1989 | Roi du Maroc, II. | |
| 4,858,617 A | 8/1989 | Sanders | |
| 4,949,725 A | 8/1990 | Raviv et al. | |
| 4,974,598 A * | 12/1990 | John | 600/509 |
| 4,989,611 A | 2/1991 | Zanetti et al. | |
| 4,991,580 A | 2/1991 | Moore | |
| 4,991,587 A | 2/1991 | Blakeley et al. | |
| 5,020,540 A | 6/1991 | Chamoun | |
| 5,038,791 A * | 8/1991 | Collins et al. | 600/509 |
| 5,042,499 A | 8/1991 | Frank et al. | |
| 5,086,776 A | 2/1992 | Fowler, Jr. et al. | |
| 5,151,856 A * | 9/1992 | Halmann et al. | 600/508 |
| 5,161,539 A | 11/1992 | Evans et al. | |
| 5,205,295 A | 4/1993 | Del Mar et al. | |
| 5,263,488 A | 11/1993 | Van Veen et al. | |
| 5,297,549 A | 3/1994 | Beatty et al. | 128/642 |
| 5,311,867 A | 5/1994 | Kynor | |
| 5,311,873 A * | 5/1994 | Savard et al. | 600/508 |
| 5,343,870 A * | 9/1994 | Gallant et al. | 600/524 |
| 5,433,198 A | 7/1995 | Desai | |
| 5,433,209 A | 7/1995 | Gallant et al. | |
| 5,483,968 A * | 1/1996 | Adam et al. | 600/508 |
| 5,487,391 A | 1/1996 | Panescu | |
| 5,503,149 A | 4/1996 | Beavin | |
| 5,503,158 A | 4/1996 | Coppock et al. | |
| 5,553,611 A | 9/1996 | Budd et al. | 128/642 |
| 5,568,809 A | 10/1996 | Ben-haim | |
| 5,606,978 A | 3/1997 | Armstrong et al. | |
| 5,687,737 A * | 11/1997 | Branham et al. | 600/523 |
| 5,947,899 A | 9/1999 | Winslow et al. | 600/410 |
| 6,014,582 A | 1/2000 | He | 600/544 |
| 6,052,618 A | 4/2000 | Dahlke et al. | 600/523 |
| 6,236,886 B1 | 5/2001 | Cherepenin et al. | 600/547 |
| 6,238,886 B1 | 5/2001 | Patel et al. | |
| 2004/0181160 A1 | 9/2004 | Rudy | 600/509 |

OTHER PUBLICATIONS

Liu, Zhiwei W., Inverse Reconstruction of Endocardial Potentials, Electrograms and Activation Sequences from Intracavitary Probe Potential Measurements, Master's Thesis, Dept. of Biomedical Engineering, Case Western Reserve University, Aug., 1996, pp 1–121.

Jia, Ping, Noncontact Catheter for Electrophysiological Cardiac Mapping, Master's Thesis, Dept. of Biomedical Engineering, Case Western Reserve University, Jan., 1998, pp. 1–57.

Jia, Ping et al., Endocardial Mapping of Electrophysiologically Abnomal Substrates and Cardiac Arrhythmias Using a Noncontact Nonexpandable Catheter, J Cardiovasc Electrophysiol, vol. 13, Sep., 2002, pp. 888–895.

Liu, Zhiwei W. et al., Noncontact Endocardial Mapping: Reconstruction of Electrograms and Isochrones From Intracavitary Probe Potentials, J Cardiovasc Electrophysiol, vol. 8, Apr., 1997, pp. 415–431.

Khoury, Dirar S. et al, A Model Study of Volume Conductor Effects on Endocardial and Intracavitary Potentials, Circulation Research, vol. 71, 1992, pp. 511–525.

Liu, Zhiwei W. et al., Endocardial Potential Mapping from a Noncontact Nonexpandable Catheter: A Feasibility Study, Annals of Biomedical Engineering, 1998, vol. 26, pp. 994–1009.

Khoury, Dirar S. et al., Reconstruction of Endocardial Potentials and Activation Sequences From Intracitary Probe Measurements, Circulation, 1995, vol. 91, pp. 845–863.

Rudy Y., "The Inverse Problem in Electrocardiography Solutions in Terms of Epicardial Potentials": CRC Critical Reviews in Biomedical Engineering, 16:215–288 (1988).

Rudy, Y., et al. , "The Electrocardiographic Inverse Problem," Critical Reviews in Biomedical Engineering, 20:25–48 (1992).

Messinger, et al., "Computational Issues of Importance to the Inverse Recovery of Epicardial Potentials in a Realistic Heart–Torso Geometry," Math Biosci, 97:85–120 (1989) (published erratum in Math Biosci 99(1): 141 (Apr. 1990).

Oster, et al., "The Use of Temporal Information in the Regularization of the Inverse Problem of a Electrocardiography," IEEE Transactions on Biomedical Engineering, 39:65–75 (1992).

Messinger, et al. , "Regularization of the Inverse Problem in Electrocardiography: A Model Study, " Mathematical Biosciences 89:79–118 (1988).

P. Colli Franzone, et al., "A Mathematical Procedure for Solving the Inverse Potential Problem of Electrocardiography," Mathematical Biosciences 77:353–396 (1985).

P. Colli Franzone, et al., "Finite Element Approximation of Regularized Solutions of the Inverse Potential Problem of Electrocardiography and Applications to Experimental Data", Calcolo 22:91–186 (1985).

Taccardi, et al., "Effect of Myocardial Fiber Direction on Epicardial Potentials", Circulation, 90:3076–90(1994).

Rudy, Y., et al., "Noninvasive Electrocardiographic Imaging," Annals of Noninvasive Electrocardiography, vol. 4, No. 3, Jul. 1999 (Futura Publishing Company, Inc., Armonk, NY).

Oster, et al., "Noninvasive Electrocardiographic Imaging—Reconstruction of Epicardial Potentials, Electrograms, and Isochones and Localization of Single and Multiple Electrocardiac Events", Circulation, vol. 96, No. 3, Aug. 5, 1997.

Oster, et al., "Electrocardiographic Imaging—Noninvasive Characterization of Intramural Myocardial Activation From Inverse–Reconstructed Epicardial Potentials and Electrograms", Circulation, 1998; 97, Apr. 21, 1998, pp. 1496–1507.

Oster, et al., "Electrocardiographic Imaging of Electrophysiologically Abnormal Substrates In Infarcted Hearts—A Model Study", Circulation, 2000; 101, Feb. 8, 2000, pp. 533–540.

Rudy, Y., et al., "Noninvasive Imaging and Catheter Imaging of Potentials, Electrograms, and Isochones on the Ventricular Surfaces," Journal of Electrocardiology, vol. 30 Supplement (1998) pp. 19–23.

Oster, et al., "Regional Regularization of the Electrocardiographic Inverse Problem: A Model Study Using Spherical Geometry," IEEE Transactions on Biomedical Engineering, vol. 44, No. 2, Feb. 1997, pp. 188–199.

Burnes, J., et al., "A Field–Compatible Method for Interpolating Biopotentials", Annals of Biomedical Engineering, vol. 26, pp. 37–47, 1998.

Burnes, J., et al., "A Noninvasive Imaging Modality for Cardiac Arrhythmias", Circulation, vol. 2102, No. 17, Oct. 24, 2000, pp. 2152–2158.

Ramanathan, C., et al., "Electrocardiographic Imaging: I. Effect of Torso Inhomogeneities on Body Surface Electrocardiographic Potentials", Journal of Cardiovascular Electrophysiology, vol. 12, No. 2, Feb. 2001, pp. 229–240.

Ramanathan, C., et al., "Electrocardiographic Imaging: II. Effect of Torso Inhomogeneities on Noninvasive Reconstruction of Epicardial Potentials, Electrograms, and Isochrones", Journal of Cardiovascular Electrophysiology, vol. 12, No. 2, Feb. 2001, pp. 241–252.

Burnes, J., et al., "Imaging Dispersion of Myocardial Repolarization, I Comparison of Body–Surface and Epicardial Measures", Circulation, vol. 104, No. 11, Sep. 11, 2001, pp. 1299–1305.

Ghanem, R., et al., "Imaging Dispersion of Myocardial Repolarization, II Noninvasive Reconstruction of Epicardial Measures", Circulation, vol. 104, No. 11, Sep. 11, 2001. pp. 1306–1312.

Ghanem, R., et al., "Electrocardiographic Imaging: Noninvasive Reconstruction of Epicardial Measures of Dispersion of Repolarization," Biomedizinische Technik. vol. 46, Supp. 2, 2001, pp. 201–203.

Burnes, J., et al., "Noninvasive ECG Imaging of Substrate and Intramural Ventricular Tachycardia in Infarcted Hearts," Journal of the American College of Cardiology, Dec., 2001, in press.

Tikhonov, A., et al., "Solutions of Ill–Posed Problems", Chapter II. "The Regularization Method", 1977 V.H. Winston & Sons, Washington, D.C., A Halsted Press, John Wiley & Sons, pp. 45–62.

Brebbia, C., et al., "Boundary Element Techniques—Theory and Applications in Engineering", Springer–Verlag, 1984, pp. 127–137.

Brebbia, C., et al., "Boundary Elements An Introductory Course," Computational Mechanics Publications, Southampton, Boston, pp. 87–90.

Jackson, John D., "Classical Electrodynamics," Second Edition, John Wiley & Sons, pp. 39–43.

Oster, H.S., Taccardi, B., Lux, R.L., Ershler, P.R., Rudy, Y., "Noninvasive Electrocardiographic Imaging—Reconstruction of Epicardial Potentials, Electrograms, and Isochrones and Localization of Single and Multiple Electrocardiac Events", Circulation, vol. 96, No. 3, Aug. 5, 1997.

Oster, H.S., Taccardi, B., Lux, R.L., Ershler, P.R., Rudy, Y., "Electrocardiographic Imaging—Noninvasive Characterization of Intramural Myocardial Activation From Inverse–Reconstructed Epicardial Potentials and Electrograms", Circulation, 1998;97, Apr. 21, 1998, pp. 1496–1507.

Burnes, J.E., Taccardi, B., MacLeod, R.S., Rudy, Y., "Noninvasive ECG Imaging Of Electrophysiologically Abnormal Substrates inInfarcted Hearts—A Model Study", Circulation, 2000;101,Feb. 8, 2000, pp. 533–540.

Rudy Y, Taccardi B, Noninvasive Imaging and Catheter Imaging of Potentials, Electrograms, and Isochrones on the Ventricular Surfaces, Journal of Electrocardiology, vol. 30 Supplement, (1998) pp. 19–23.

Oster HS, Rudy Y, "Regional Regularization of the Electrocardiographic Inverse Problem: A Model Study Using Spherical Geometry", IEEE Transactions on Biomedical Engineering, vol. 44, No. 2, Feb. 1997, pp. 188–199.

Burnes JE, Kaelber DC, Taccardi B, Lux RL, Ershler PH, Rudy Y, "A field–Compatible Method For Interpolating Biopotentials", Annals of Biomedical Engineering, vol. 26, pp. 37–47, 1998.

Burnes, JE, Taccardi, B., Rudy, Y., "A Noninvasive Imaging Modality for Cardiac Arrhythmias", Circulation vol. 102, No. 17, Oct. 24, 2000, pp. 2152–2158.

Ramanathan, C., Rudy, Y., "Electrocardiographic Imaging: I. Effect of Torso Inhomogeneities on Body Surface Electrocardiographic Potentials", Journal of Cardiovascular Electrophysiology, vol. 12, No. 2, Feb. 2001, pp. 229–240.

Ramanathan, C., Rudy, Y., "Electrocardiographic Imaging: II. Effect of Torso Inhomogeneities on Noninvasive Reconstruction of Epicardial Potentials, Electrograms, and Isochrones", Journal of Cardiovascular Electrophysiology, vol. 12, No. 2, Feb. 2001, pp. 241–252.

Burnes, JE., Ghanem, RN., Waldo, AL., Rudy, Y., "Imaging Dispersion of Myocardial Repolarization, I. Comparison of Body–Surface and Epicardial Measures", Circulation, vol. 104, No. 11, Sep. 11, 2001, pp. 1299–1305.

Burnes, JE., Ghanem, RN., Waldo, AL., Rudy, Y., "Imaging Dispersion of Myocardial Repolarization, II. Noninvasive Reconstruction of Epicardial Measures", Circulation, vol. 104, No. 11, Sep. 11, 2001, pp. 1306–1312.

Ghanem, RN., Burnes, JE., Waldo, AL., Rudy, Y., "Electrocardiographic Imaging: Noninvasive Reconstruction of Epicardial Measures of Dispersion of Repolarization", Biomedizinische Technik, vol. 46, Suppl.. vol. 2, 2001, pp. 201–203.

Burnes, JE., Taccardi, B., Ershler, PR., Rudy, Y., "Noninvasive ECG Imaging of Substrate and Intramural Ventricular Tachycardia in Infarcted Hearts", Journal of the American College of Cardiology, Dec., 2001, in press.

Tikhonov, A.N., Arsenin, V.Y., "Solutions of Ill–Posed Problems", Chapter II. "The Regularization Method", 1977 V.H. Winston & Sons, Washington, D.C., A Halsted Press , John Wiley & Sons, pp. 45–62.

Brebbia, C.A., Telles, J.C.F., Wrobel, L.C., "Boundary Element Techniques—Theory and Applications in Engineering", Springer–Verlag, 1984, pp. 127–137.

Brebbia, C.A., J. Dominguez, "Boundary Elements, An Introductory Course", Computational Mechanics Publications, Southampton, Boston, pp. 87–90.

Jackson, J.D., "Classical Electrodynamics", Second Edition, John Wiley & Sons, pp. 39–43.

Rudy Y, Messinger–Rapport BJ, The inverse problem in electrocardiography solutions in terms of epicardial potentials,: CRC Crit Rev Biomed Eng., 16:215–268 (1988).

Rudy Y, Oster HS, "The electrocardiographic inverse problem, " CRC Crit Rev Biomed Eng., 20:25–46 (1992).

Messinger–Rapport BJ, Rudy Y, "Computational issues of importance to the inverse recovery of epicardial potentials in a realistic heart–torso geometry," Math Biosci, 97:85–120 (1989) (published erratum in Math Biosci, 99(1):141 (Apr. 1990)).

Oster HS, Rudy Y, "The use of temporal information in the regularization of the inverse problem of a electrocardiography," IEEE Trans Biomed Eng., 39:65–75 (1992).

Messinger, Rapport BJ, Rudy Y, "Regularization of the inverse problem in electrocardiography. A model study," Math Biosci, 89:79–118 (1988).

Colli–Franzone P., Guerri L., Taccardi B., Viganotti C., "Mathematical procedure for solving the inverse problem of electrocardiography," Math Biosci, 77:353–96 (1985).

Colli–Franzone P., Guerri L., Taccardi B., Viganotti C., "Finite element approximation of regularized solutions of the inverse potential problem of electrocardiography and applications to experimental data", Calcolo 1985, 22:91–186.

Taccardi, Macchi, "Effect of myocardial fiber direction on epicardial potentials," *Circulation*, 90:3076–90 (1994).

Rudy, Y., Burnes, J.E., "Noninvasive Electrocardiographic Imaging," *Annals of Noninvasive Electrocardiology*, vol. 4, No. 3, Jul. 1999 (Futura Publishing Company, Inc., Armonk, NY).

* cited by examiner

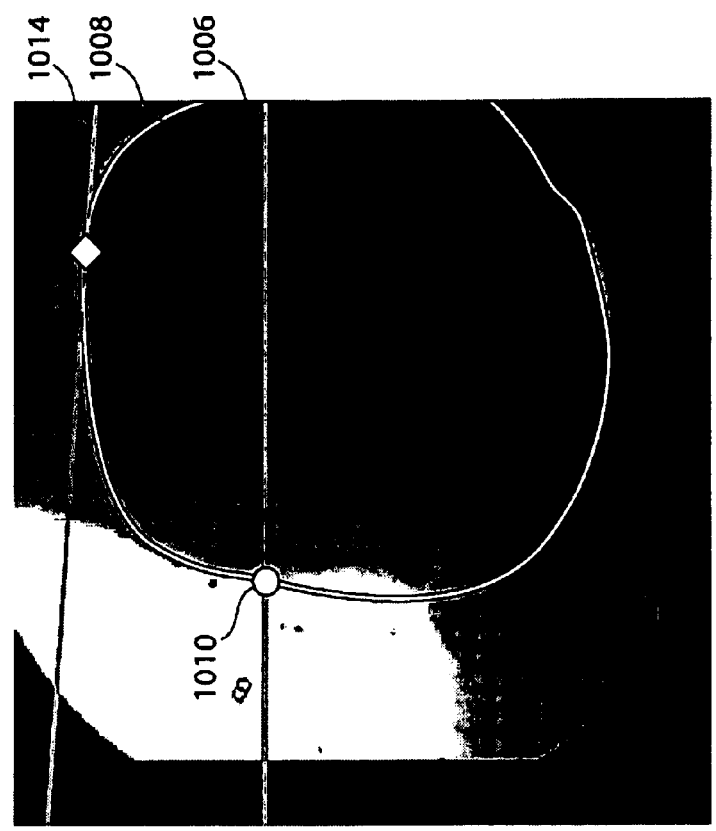
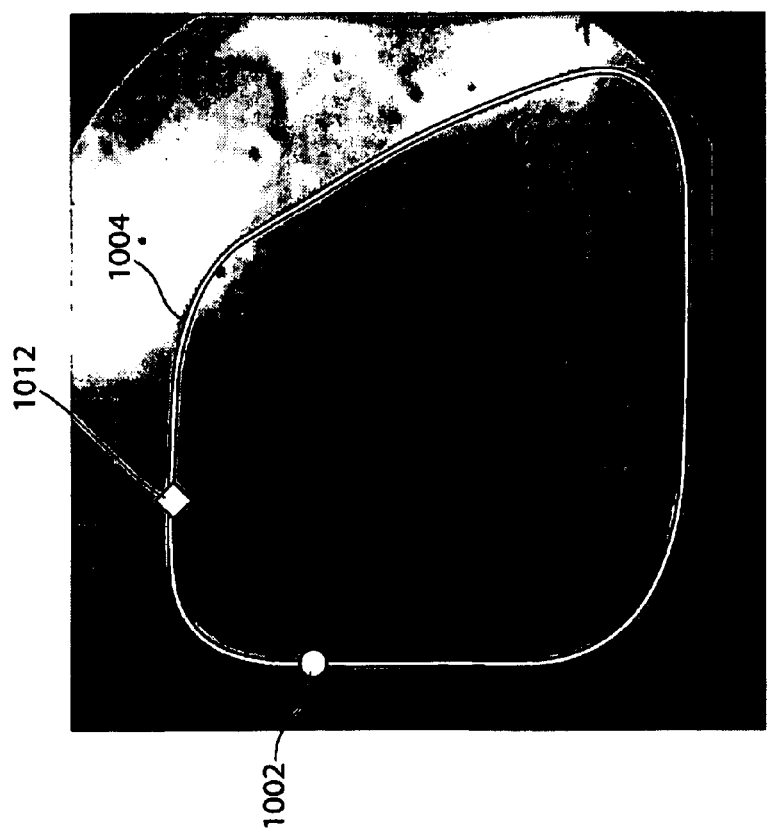
Fig. 10B
Fig. 10A

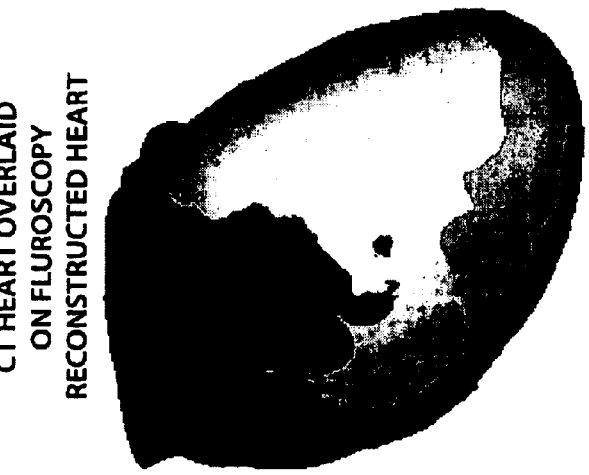
Fig. 13C CT HEART OVERLAID ON FLUROSCOPY RECONSTRUCTED HEART
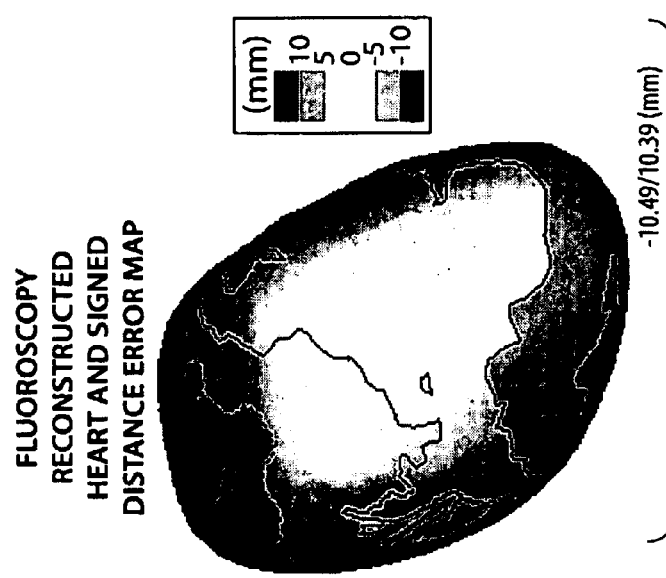
Fig. 13B FLUOROSCOPY RECONSTRUCTED HEART AND SIGNED DISTANCE ERROR MAP −10.49/10.39 (mm)
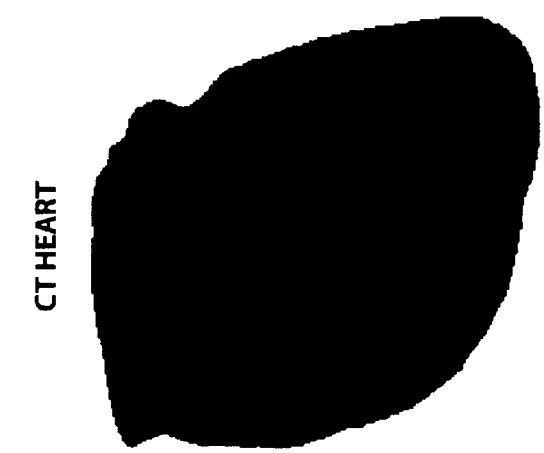
Fig. 13A CT HEART

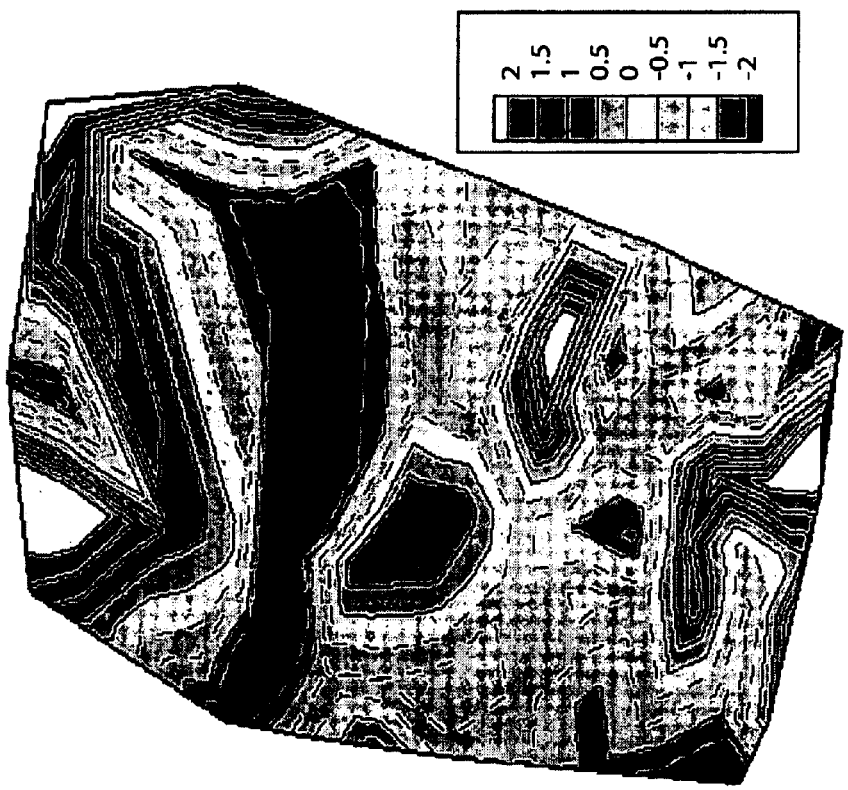
Fig. 14B
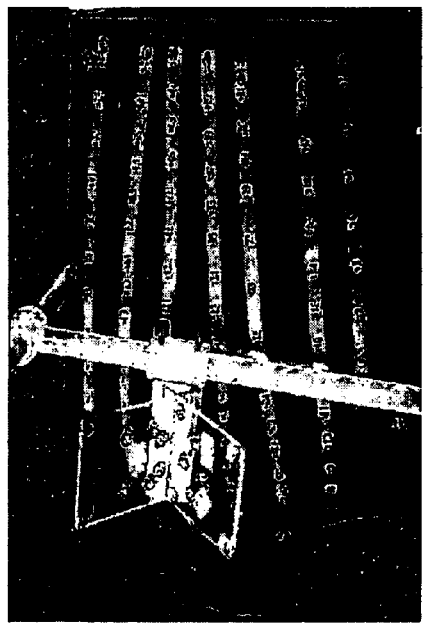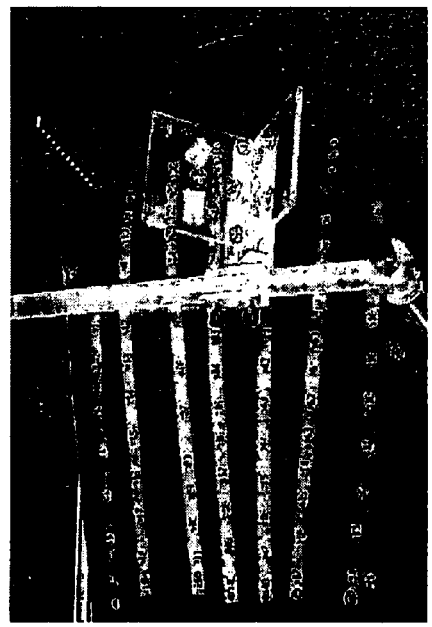
Fig. 14A

BODY SURFACE POTENTIALS

MEASURED

GMRes

Tikhonov

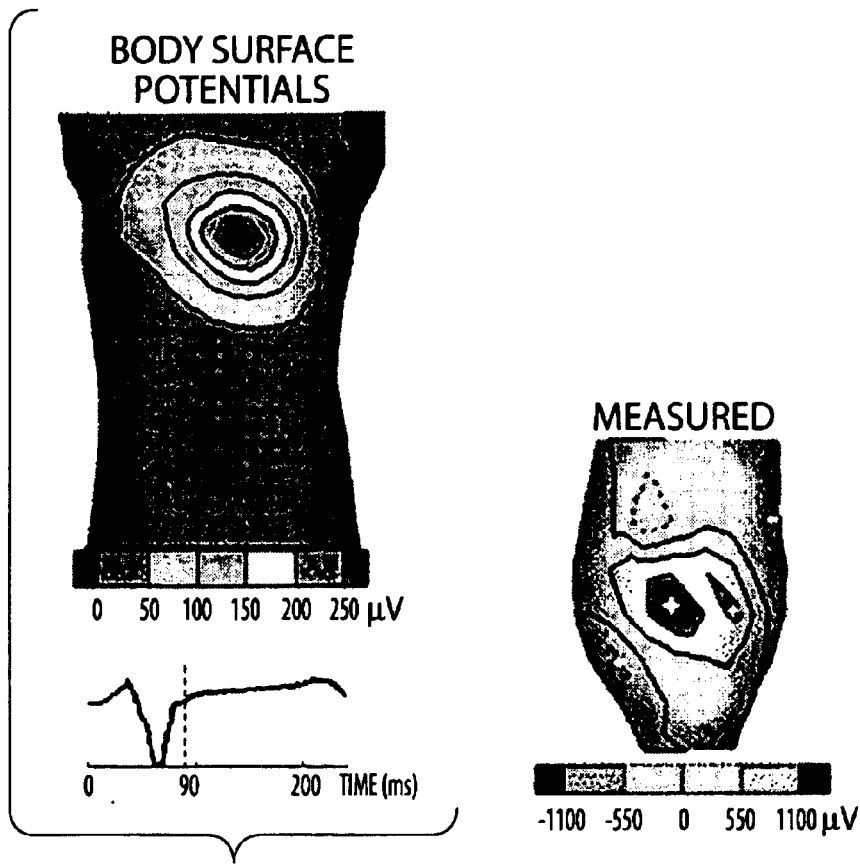
Fig. 20B-1
Fig. 20B-2
Fig. 20B-3
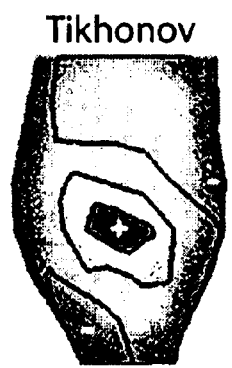
Fig. 20B-4

SYSTEMS AND METHODS FOR DETERMINING A SURFACE GEOMETRY

CLAIM OF PRIORITY

This application is a continuation-in-part to U.S. Ser. No. 10/264,572, filed Oct. 4, 2002, entitled "Systems And Methods For Noninvasive Electrocardiographic Imaging (ECGI) Using Generalized Minimum Residual (GMRES)," naming Yoram Rudy, Charulatha Ramanathan, Raja Ghanem, and Ping Jia as inventors, where U.S. Ser. No. 10/264,572 claims priority to U.S. Ser. No. 60/327,419, entitled "Noninvasive Electrocardiographic Imaging (ECGI): The application of the Generalized Minimal Residual (GMRes) Method," filed on Oct. 4, 2001, naming Yoram Rudy, Charulatha Ramanathan, Raja Ghanem, and Ping Jia as inventors; and, this application also claims priority to and is a continuation-in-part of U.S. Ser. No. 09/463,428, filed on Jan. 21, 2000, entitled "System And Method For Non-Invasive Electrocardiographic Imaging," naming Yoram Rudy as inventor, now abandoned, which claims priority to PCT/US98/15927, filed Jul. 29, 1998, which claims priority to U.S. Ser. No. 60/054,342, filed on 31 Jul. 1997; and this application also claims priority to and is a continuation in part of U.S. Ser. No. 10/037,603, filed on Oct. 19, 2001, now U.S. Pat. No. 6,772,004, entitled "System And Method For Non-Invasive Electrocardiographic Imaging," naming Yoram Rudy as inventor, which claims priority as a continuation of the aforementioned U.S. Ser. No. 09/463,428, where the contents of all aforementioned provisional and non-provisional U.S. and PCT applications are incorporated herein by reference in their entirety.

STATEMENT OF GOVERNMENT INTEREST

The contents of this disclosure were supported by NIH-NHLBI Grant R37 HL-33343 and ROI HL-49054 (Y.R.).

BACKGROUND (1) Field

The disclosed methods and systems relate generally to electrocardiographic imaging, and more particularly to methods and systems for modeling a surface geometry for use in, for example, electrocardiographic imaging.

(2) Description of Relevant Art

Imaging and diagnosing cardiac electrical activity can be problematic because the electrical activity is time dependent and spatially distributed throughout the myocardium. Electrocardiographic techniques that include, for example, electrocardiograms (ECG) and vectorcardiography (VCG) can be limited in their ability to provide information and/or data on regional electrocardiac activity. These methods can also fail to localize bioelectric events in the heart.

Simultaneous recordings of potentials at tens or hundreds of locations on the torso, for example, can provide body surface potential maps (BSPMs) over the torso surface. Although the BSPMs can indicate regional cardiac electrical activity in a manner that may be different from conventional ECG techniques, these BSPM techniques generally provide a comparatively low resolution, smoothed projection of cardiac electrical activity that does not facilitate visual detection or identification of cardiac event locations (e.g., sites of initiation of cardiac arrhythmias) and details of regional activity (e.g., number and location of arrythmogenic foci in the heart).

In comparison, potential distributions measured on and over the epicardial surface of the heart can provide comparatively more accurate and higher resolution data that reflects electrical events within the myocardium. Accordingly, the study of cardiac excitation and arrhythmogenesis, for example, often rely upon the mapping of potentials directly from the epicardium.

With an increasing use of nonpharmacological anti-arrhythmic interventions (e.g., ablation), comparatively rapid and accurate localization of electrocardiac events can be beneficial. Electrocardiographic imaging (ECGI) is a noninvasive imaging modality for cardiac electrophysiology (EP) and arrhythmias that can be used to reconstruct epi-cardial potentials and to provide electrograms and isoch-rones from, for example, BSPMs and/or other electrocar-diographic body surface potentials.

SUMMARY

The disclosed methods and systems can be used to determine a surface geometry of an object, where the methods and systems include determining a first projection matrix based on a first imaging device, determining a second projection matrix based on a second imaging device, obtaining at least one first two-dimensional (2D) image of the object using the first imaging device, obtaining at least one second 2D image of the object using the second imaging device, determining a contour of the object in the first 2D image and the second 2D image, and, based on the at least two contours, the first projection matrix, and the second projection matrix, reconstructing 3D data associated with the surface of the object. The first imaging device and the second imaging device may be the same imaging device, however, in one embodiment, the first and second imaging devices can include X-ray such as biplanar (or multiplanar) fluoroscopy, digital camera(s), and/or other devices from which a 2D image of the object can be obtained.

In one embodiment, the first projection matrix can be associated with the first imaging device, and the first projection matrix can thus be determined by providing at least one calibration object that includes at least six markers, employing a 3D digitizing instrument to associate 3D data with the at least six markers, providing a first calibration image using the first imaging device, determining the image coordinates of a first at least six of the at least six markers based on the first calibration image, and, computing the first projection matrix based on the 3D data and the first calibration image coordinates. In one embodiment, the at least one calibration object can include a calibration object that can be V-shaped, and a planar board, where the calibration object and the planar board can include identifiable markers. In some embodiments, the V-shaped calibration object can be placed on a first side of the object, and the planar board can be placed on a second side of the object.

Accordingly, the second projection matrix, which can be associated with the second imaging device, can be determined by providing a second calibration image using the second imaging device, determining the image coordinates of a second at least six of the at least six markers based on the second calibration image, where the first at least six markers are the same as, correlated with, or otherwise associated with the second at least six markers, and, computing the second projection matrix based on the 3D data and the second calibration image coordinates. The first calibration image and the second calibration image can include image data based on the same markers. In such an embodiment, the methods and systems can include computing the 3D coordinates of the at least six markers based on the first projection matrix, the second projection matrix, the first image calibration coordinates of the at least six markers, and the second calibration image of the at least six markers, and, comparing the computed 3D coordinates to the 3D data associated with the at least six markers. In one example, the comparison can be further compared to a threshold. Based on the comparison, the aforementioned process of computing the first and/or second projection matrices can be re-performed, in part or in whole, by repeating the process from the use of 3D digitizing instrument to associate 3D data with the at least six markers, from the taking or otherwise obtaining a first calibration image using the first imaging device, from the taking or otherwise obtaining a second calibration image using the second imaging device, from the determining the image coordinates of the at least six markers based on the first calibration image, and/or from the determining the image coordinates of the at least six markers based on the second calibration image. The process of computing the first and second projection matrices, otherwise referred to as a calibration process, can be repeated based on the embodiment, to provide an accuracy or other measure relative to a threshold.

The methods and systems can include obtaining at least one (first and/or second) 2D image using the first imaging device and the second imaging device, where the first imaging device and the second imaging device can include X-ray, fluoroscopy, multiplanar fluoroscopy including biplanar fluoroscopy, a digital camera, and other digital imaging devices and/or means. The obtaining of a (first and/or second) 2D image can also include selecting a 2D image based on a comparatively enlarged projection of the object. For example, when the object is a heart, the first and second 2D images can be selected to correspond to a time when the heart is enlarged to a comparatively largest size during a cardiac cycle. In some embodiments, the first and second 2D images can be obtained simultaneously to provide two views of the object at the same time, however, in some embodiments, the first and second 2D images can be collected sequentially.

The disclosed methods and systems also include determining a contour based on the first 2D image(s) and the second 2D image(s), where the contour can be based on a user provided designation and/or an automatic computation. Determining a contour can thus include providing a number of points to include in the contour, extrapolating to provide a contour having a designated number of points, and/or displaying the contour in at least one of the first 2D image and the second 2D image. The number of points in the contour can be provided by a user or another, and thus can be variable or fixed.

The reconstructing of 3D data can thereby include generating matching contour point pairs based on points in the contour, the first projection matrix, and the second projection matrix. The matching contour point pairs can be computed based on a fundamental matrix, where the fundamental matrix can be based on the first projection matrix and the second projection matrix. The matching contour point pairs can also be based on determining a smallest eigenvalue of the fundamental matrix.

The 3D reconstruction can include weighting reconstructed points from a matching contour point pair, where the weights can be based on a distance from a line defined by a first focal point associated with the first imaging device, and a second focal point associated with the second imaging device. Weights can be based on a distance from a centroid, for example. In one embodiment, the weights can include a weight of 0.1 for a reconstructed point furthest from the line, and a weight of 0.3 otherwise.

The 3D reconstruction can also include forming a meshed surface based on the first projection matrix, the second projection matrix, and at least one matching contour point pair based on the at least two contours. The 3D data reconstruction can include creating splines (e.g., b-splines) based on 3D points reconstructed from the first projection matrix, the second projection matrix, and at least one matching contour point pair based on the at least two contours. In one embodiment, the spline data can be converted to spherical coordinates. In some embodiments, the spline can be extrapolated and/or fitted, where the fitting can be based on a bicubic spline least squares fit, although other least squares and/or other fitting techniques can be used. In some embodiments, the 3D data can be converted to Cartesian coordinates.

The methods and systems include projecting the 3D points onto a unit sphere centered at the centroid of the 3D points, computing a convex hull, extracting connectivity data from the convex hull, and forming a meshed surface based on the 3D points and the connectivity data, where the meshed surface can be associated with the surface geometry of the object. The meshed surface can thus be registered to/with a second object surface, and, a boundary element method can be employed to determine the geometry between the object surface and the second object surface.

In one embodiment, the object surface is a heart surface, and the second object surface is an electrode vest surface. In such an embodiment, the methods and systems can be employed to determine a geometrical relationship between the outer surface of the heart (e.g., epicardial surface) and the electrode vest. Such embodiment can be used in ECGI applications.

Accordingly, also disclosed are methods and systems for computing epicardial surface electric potentials based on measured body surface electric potentials, where the methods and systems include generating a multidimensional matrix, the matrix representing at least one geometric relationship between at least one body surface electric potential measuring system and the epicardial surface, the multidimensional matrix being based on at least one first two-dimensional (2D) image of the epicardium using a first imaging device, at least one second 2D image of the epicardium using a second imaging device, a first projection matrix associated with the first imaging device, a second projection matrix associated with the second imaging device, a computed contour of the outer surface of the heart formed from contours identified in the at least one first 2D image and the at least one second 2D image, a computed contour of the electric potential measuring system, and, a boundary element method based on the computed contour of the outer surface of the heart and the computed contour of the electric potential measuring system. The method and system can also include using a Generalized Minimum Residual (GMRes) method to estimate an inverse of the multidimensional matrix, and, based on the inverse matrix and the measured body surface potentials, determining the epicardial surface electric potentials.

The methods and systems can thus include measuring the position of the at least one body surface electric potential measuring system, and determining a number of iterations for the GMRes method, which can also include providing a maximum number of iterations for the GMRes method, and based on the data from the maximum number of iterations, determining a number of iterations for the GMRes method. Determining a number of iterations can include comparing residual error to a Hessenberg matrix condition, and computing at least one of a corner of a condition L curve and a maximum curvature of a condition L curve. Determining a number of iterations can include determining a number of iterations based a corner of a condition L curve, a corner of an L curve, an increase in spatial frequency of a reconstructed potential map, and/or an increase in amplitude of a solution norm.

The GMRes method can include providing an initial condition of zero, and/or providing an initial condition based on a Tikhonov regularization of the multidimensional matrix.

Other objects and advantages will become apparent hereinafter in view of the specification and drawings.

BRIEF DESCRIPTION OF THE DRAWINGS

FIG. 7b illustrates one exemplary embodiment for calibrating a system according to FIG. 7a;

FIGS. 10a 10b include RAO 40° (View 1, left) and LAO 50° (View 2, right) views of acquired biplane fluoroscopy images;

FIG. 13, panel A, includes a CT heart; panel B includes a signed distance error map; and, panel C includes a CT heart overlaid with signed distance error map.

FIG. 14 demonstrates localization of torso electrode positions using photography. Panel A, includes stereo photographs of a mannequin with a calibration object (transparent structure); panel B includes a signed distance error map for reconstructed electrode locations relative to measured locations.

FIGS. 20a and 20b present epicardial potentials generated by simultaneous pacing from two closely spaced sites (e.g., 2.5 cm apart), during activation and repolarization, respectively;

DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the disclosed systems or methods.

The disclosed methods and systems can be used to determine a surface geometry, such as a heart surface geometry, which can be thereafter used to determine a geometrical relationship between the surface of the heart organ and positions of electrodes that can be placed on the body surface of a subject for which electrocardiographic imaging data is collected. In one example, the determined geometric relationship facilitates the reconstruction of epicardial electrical potentials based on electrocardiographic image (ECGI) data, where the ECGI data is derived from body surface potential maps (BSPMs). The reconstructed epicardial potentials can be used to provide electrograms and isochrones. Those of ordinary skill in the art will recognize, however, that the methods and systems are not limited to BSPMs, and/or can employ electrocardiographic data, vectorcardiogram data, or combinations thereof, and although the disclosed methods and systems present electrograms and isochrones, other and/or additional data representations can be implemented.

Figure 1:
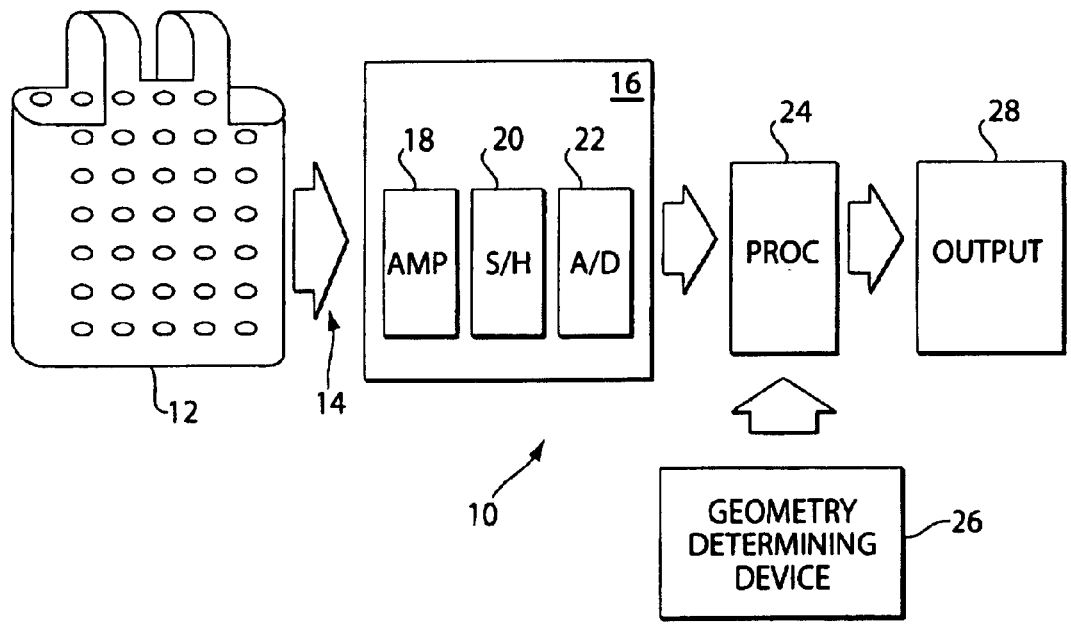
FIG. 1 illustrates a block diagram for obtaining data from an electrode vest.

FIG. 1 provides one illustration of a system according to the disclosed methods.

The FIG. 1 system 10 includes one exemplary electrode vest 12 that can include electrodes that are disposed and/or positioned within the vest 12 to provide measurements of electrical potentials across a torso (front, back, sides, etc.) when positioned on a patient, for example. The vest 12 can be connected 14 to a device 16 that can include a processor and/or circuitry (e.g., hardware and/or software) for receiving data and processing data from the vest 12 via the connection 14. In the illustrated system, the device 16 includes an amplifier 18, a sample and hold 20, and analog to digital converter 22. As provided herein, those of ordinary skill will recognize that the device 16 may be incorporated with the vest 12 in some embodiments. In the FIG. 1 system, the device 16 can provide or otherwise communicate data to a processor 24 or processor-controlled device, as provided herein. Further, the illustrated processor 24 can receive data from a geometry determining device 26. The processor 24 can include instructions and/or be coupled with hardware for processing the data from the vest 12 and the geometry determining device 26 as provided herein, and additionally and optionally can communicate such processed data to one or more output devices 28. Those of ordinary skill will recognize that the output device 28 can be a display, printer, and/or other device that can be integrated with or otherwise be in communications with the processor 24.

In an embodiment, the FIG. 1 system 10 can be an online and/or integrated channel system that can be a stand-alone and portable unit with data acquisition and data processing capabilities. Further, in one embodiment, the illustrated vest 12 can include approximately two-hundred forty silver/silver chloride (Ag/AgCl) electrodes for acquiring electrocardiograph (ECG) signals from a body surface such as a torso. Those of ordinary skill will recognize that the vest 12 can include other numbers of electrodes, including for example, in the range from approximately one-hundred twenty to two-hundred fifty, although fewer or more electrodes can be used depending upon the application. Further, although the use of silver/silver chloride electrodes allows the electrodes to be used without gel and thus may decrease the number of electrodes that may short circuit and may allow for rapid application of the electrodes to the patient, other systems that utilize gel and/or other non-gel systems can be used.

The illustrated vest 12 may also provide two-dimensional stability to the electrode array so that electrode spacing can be maintained substantially constant and electrode positions can be determined as provided herein. The vest 12, connector 14, and/or device 16 can further include comparatively high-input resistance amplifiers (e.g., on the order of $10^{12}$ ohm) and driven shield electrode cables to provide increased common mode rejection. For example, in one embodiment, driven shield cables can be coaxial cables that can be optically coupled to avoid shock to the patient, while other types of electrode arrangements and/or methods and systems to obtain body surface potentials may be used. Those of ordinary skill will thus understand the vest 12, connector 14, and device 16 to more generally be a body surface potential measurement system and/or device that provides or otherwise communicates (e.g., via wired or wireless network, direct communications, etc.) body surface potential data to the processor 24, where such data can be in a format that is compatible for receipt by the processor 24. In an embodiment, the illustrated body surface potential measurement system 12, 14, 16 can be employed for body surface mapping, epicardial mapping (e.g., using epicardial electrodes), endocardial mapping, and/or intracavitary mapping using a multi-electrode probe.

Figure 2:
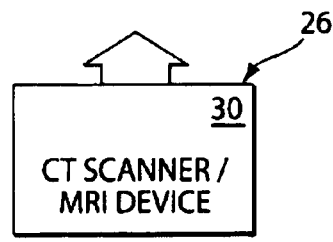
FIG. 2 illustrates one geometry determining device.

Referring again to FIG. 1, the geometry determining device 26 can be a system and/or device for providing geometric data for an anatomical part(s) such as the heart, and accordingly, the device 26 can include a system that provides x-ray, ultrasound, computed tomography (CT), and/or magnetic resonance imaging (MRI) data. For example, as shown in FIG. 2, the geometry determining device 26 can be a fluoroscopy device 30. In an embodiment according to FIGS. 1 and 2, the illustrated fluoroscopy device 30 can generate data, which can be image data, to determine torso geometry and, consequently, body surface electrode positions. The device 30 can also provide data associated with an epicardial envelope surrounding the heart, where those of ordinary skill understand that the epicardial envelope can provide an estimate of the epicardial surface. Further, locating the epicardial envelope or surface can include determining or otherwise providing data to be associated with the location of the heart. In an exemplary system that utilizes a fluoroscopy device 30, the scanner 30 can provide slice thickness between one and eight millimeters and can have adjustable kVp and mAs settings to perform different types of CT scans of different parts of a patient's body.

Figure 4:
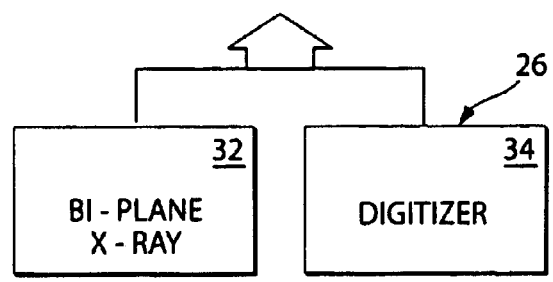
FIG. 4 illustrates other geometry determining devices.
Figure 3:
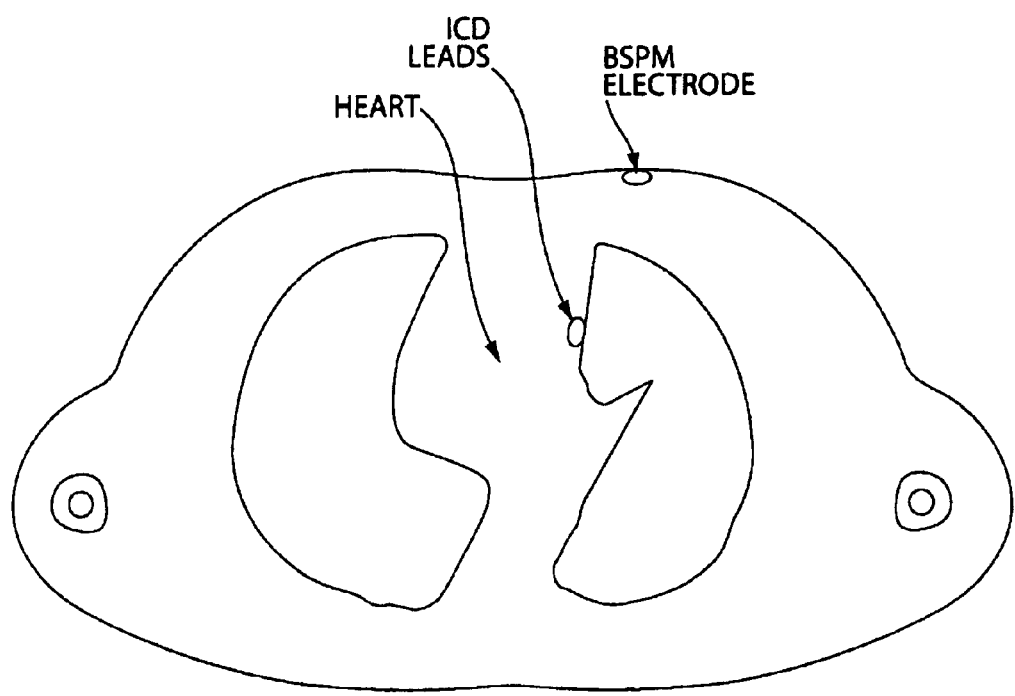
FIG. 3 illustrates a CT scan.

FIG. 4 presents an embodiment having a geometry device 26 that includes a system that includes a bi-plane or single plane x-ray fluoroscopy machine 32 and a digitizer 34. The FIG. 4 embodiment can utilize a three dimensional digitizer/locator 34 to obtain a patient's torso geometry and/or positions of body surface electrodes. In a system according to FIG. 4, an epicardial envelope can be constructed from two bi-planar x-rays using curve fitting techniques, although other techniques can be used.

Figure 5A:
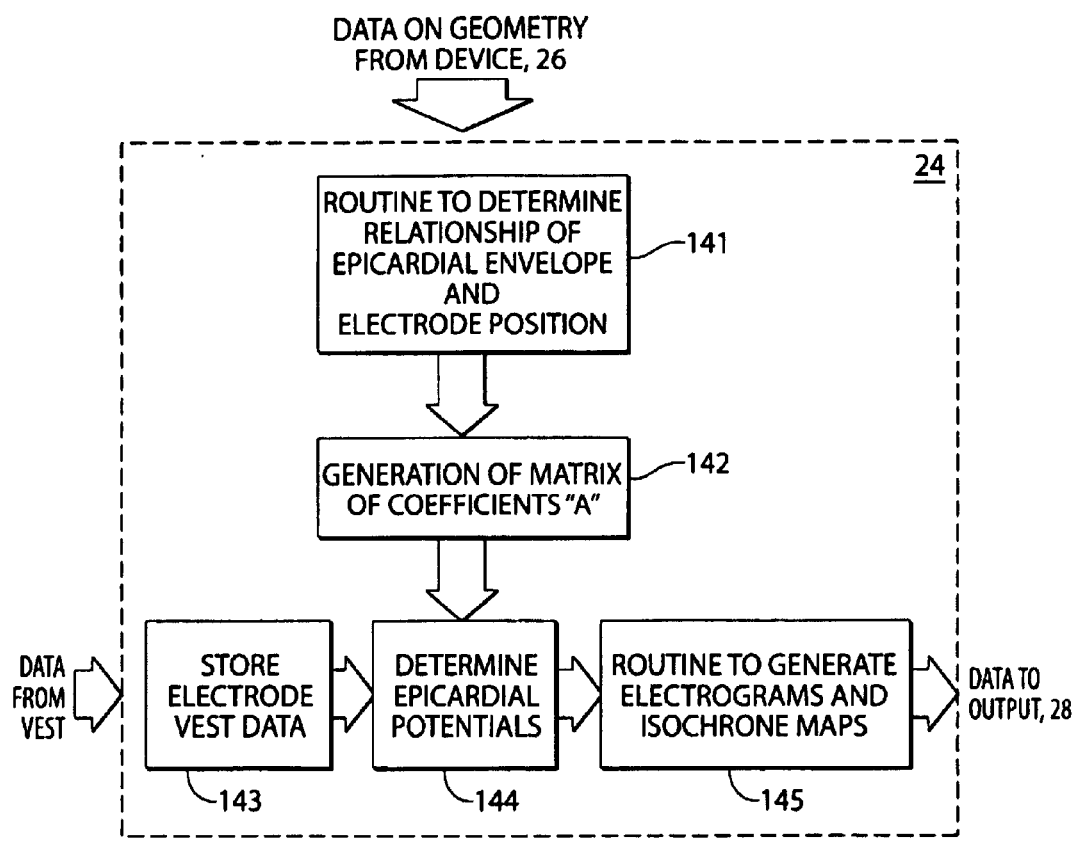
FIG. 5a is an exemplary block diagram for determining epicardial potentials.

FIG. 5(a) provides one illustrative embodiment for a processor 24 according to FIG. 1. Accordingly, in an embodiment based on FIG. 1, the geometry determining device 26 can provide the processor 24 with data associated with the geometry of the torso and vest, including for example electrode position, and the epicardial envelope (or surface). As provided herein, the geometry determining device (e.g., fluoroscopy device 30) can provide data for determining or otherwise provide data associated with a geometric envelope that approximates the epicardium to allow or otherwise facilitate a geometric relationship between the epicardial envelope surrounding the heart and electrode positions (or torso geometry) 141. In one embodiment, a matrix of coefficients, A, can also be generated 142 to express the relationship between epicardial surface and body surface. The matrix A can thus be understood to be a geometry and conductivity transfer matrix that represents properties of the volume conductor between the body surface and epicardial surface.

Referring again to FIG. 5a, electric potentials measured on the torso surface can be input to or otherwise provided to the processor 24 from the vest 12 or other device that provides electrical potentials, where in the FIG. 5a embodiment, the processor can store 143 such electrical potentials. The processor 24 can then cause epicardial potentials to be determined 144 based on the aforementioned electrical potentials and matrix of coefficients, A. As provided previously herein, based on the epicardial potentials, electrograms and isochrone maps can be generated for display and evaluation 145.

Figure 5B:
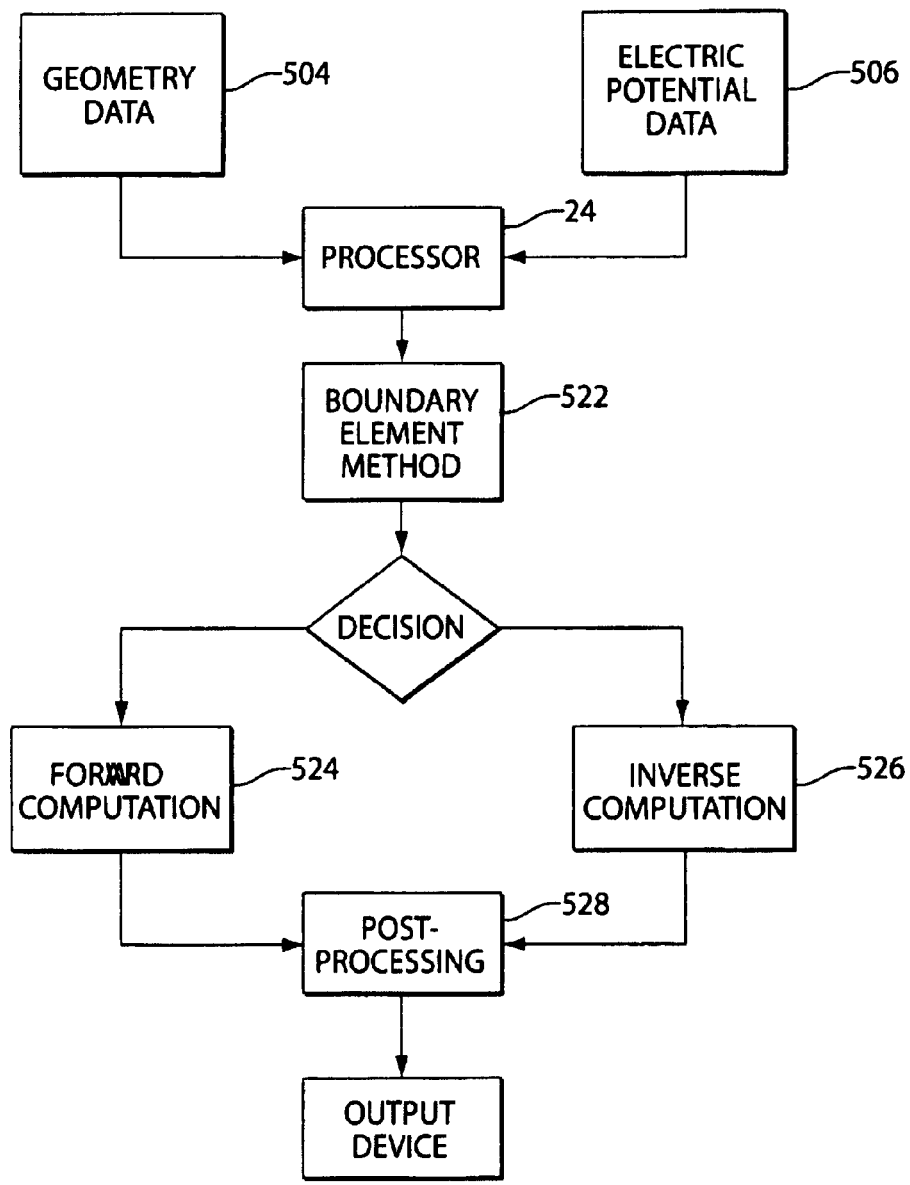
FIG. 5b is another exemplary block diagram for determining epicardial potentials.

Those of ordinary skill will recognize that the modules and/or components of FIG. 5a are merely illustrative for explanatory purposes, and such modules can be otherwise combined and/or dispersed amongst one or more processors. Accordingly, FIG. 5b includes an embodiment according to FIG. 5a where data 504 from a geometry determining device 26 and electrical potential data 506 from a body surface measuring device 12, 14, 16 can provide input 500 to the processor 24. As FIG. 5b indicates, the input data and other data can be conditionally processed and provided to a boundary element module 522. Forward computations 524, or computing torso potentials from known epicardial potentials, and/or inverse 526 computations, or computing epicardial surface potentials based on measured torso potentials, as provided herein, can employ data from the boundary element module 522. Those of ordinary skill will recognize that in clinical applications, inverse computations 526 are computed. Once the forward and/or reverse computations are performed 524, 526, output and/or post-processing 528 can be performed, and optionally, output files can be generated.

Figure 5C:
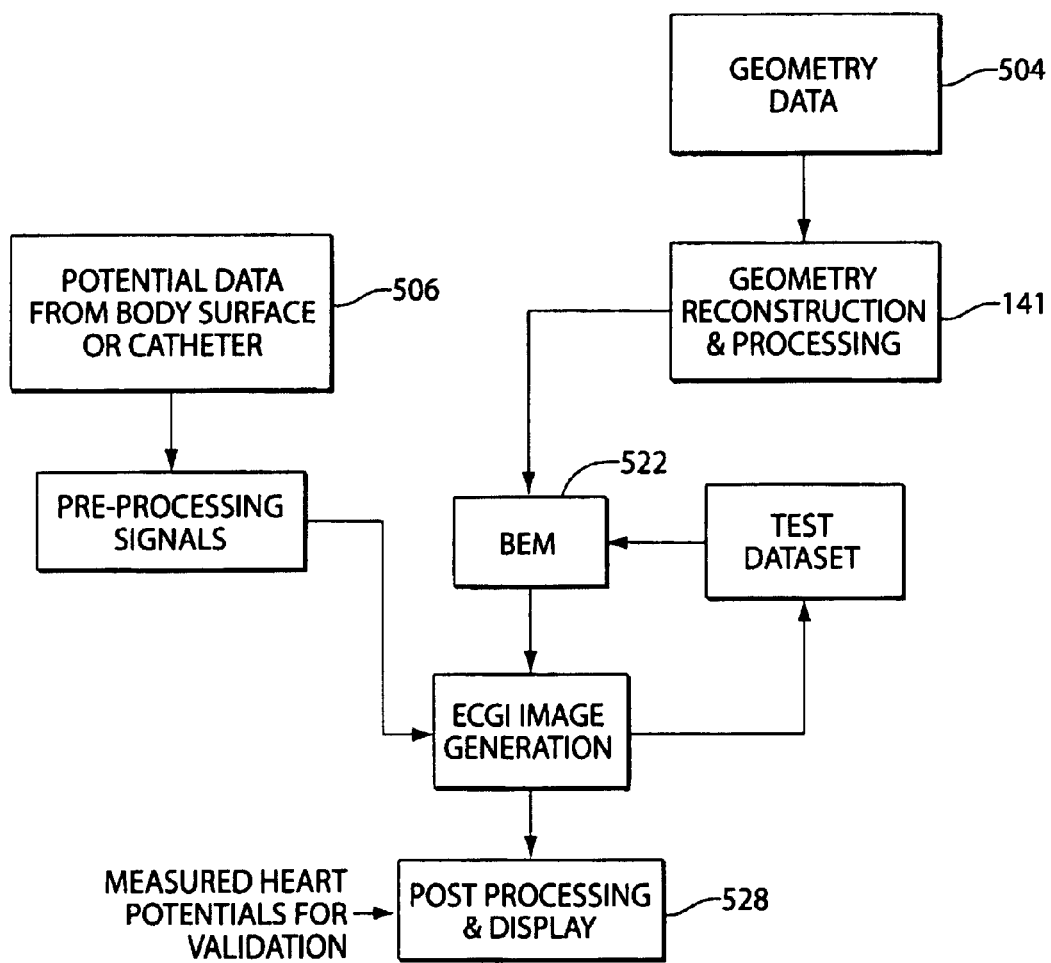
FIG. 5c is another exemplary block diagram for determining epicardial potentials

FIG. 5c provides another exemplary block diagram for determining epicardial potentials.

Figure 6:
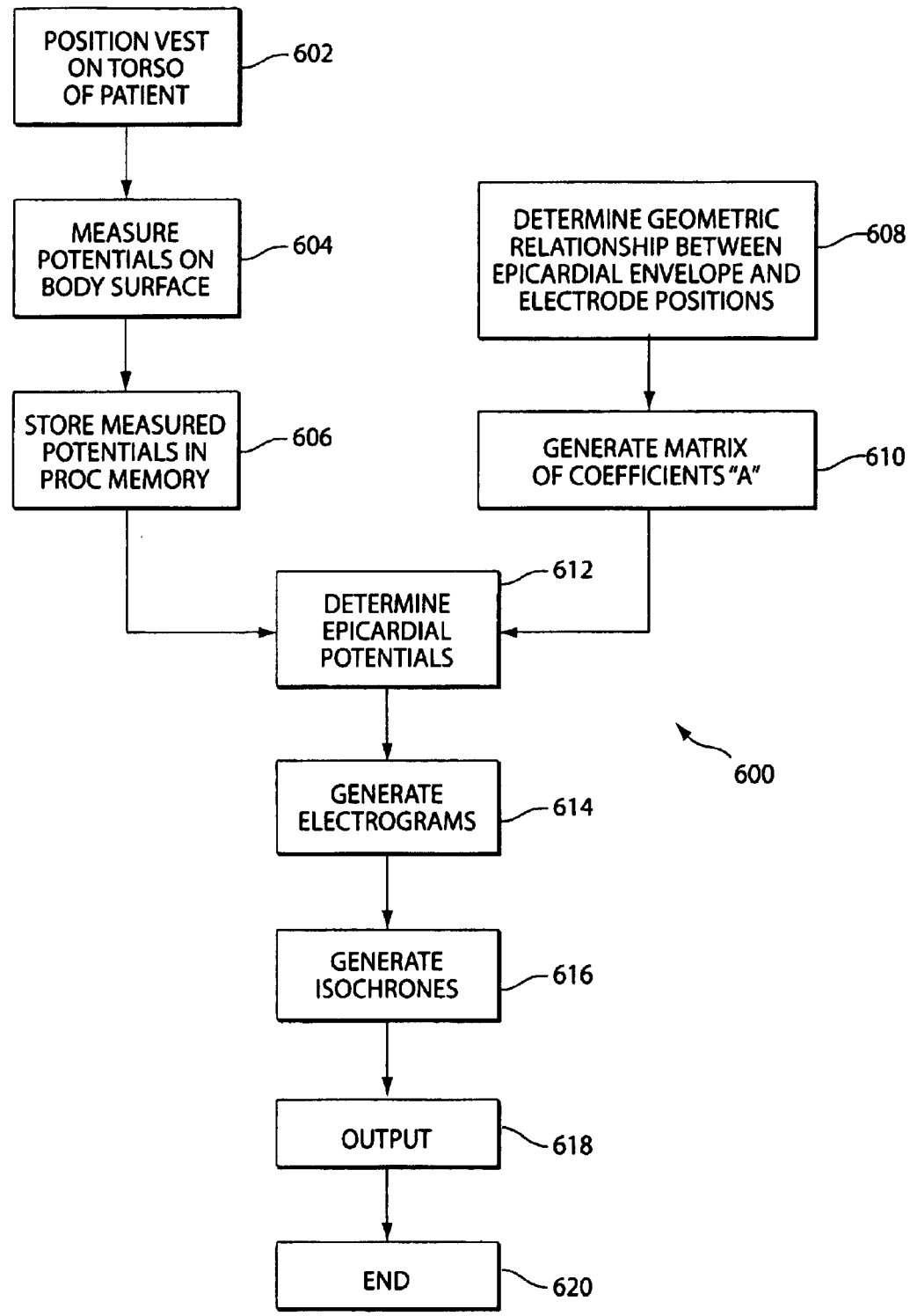
FIG. 6 is an exemplary flow diagram for determining epicardial potentials.

FIG. 6 provides another illustration 600 for one embodiment of the disclosed methods and systems for determining epicardial potentials from geometry determining device data and body surface electrical potential data. In the FIG. 6 example, an electrode vest 12 can be positioned on the torso of a human 602 to provide measurements of electrical potentials of the human's body (torso) surface 604. In the FIG. 6 embodiment, these body surface electrical potentials can be stored in a memory 606. Further, a geometry determining device 26 can be used to provide a geometric relationship between the torso geometry (e.g., electrode positions of the vest) and the human's epicardial envelope, or epicardial surface 608. Based on this geometric relationship between the vest electrodes and epicardial envelope, a matrix of coefficients, A, can be generated 610.

Accordingly, epicardial (surface) potentials, or the electrical potentials on the surface of the heart, can be determined based on the stored body surface potentials and the matrix of coefficients 612 that relates the potentials from the body surface to the epicardial surface. Electrograms and isochrones, for example, and other data representations can be generated 614, 616 based on the epicardial surface potentials, and optionally output 618 to a device 28.

Those of ordinary skill will recognize that computing torso potentials based on measured epicardial potentials (the "Forward Problem") includes solving Laplace's equation which entails the discretization of Laplace's equation (using Green's second theorem as described in, far example, Jackson J D, Classical electrodynamics, John Wiley and Sons, New York (1975)) in the volume between the epicardial surface and the body surface. A known boundary element method (BEM) (e.g., Brebbia C A, Telles J C F, Wrobel L C, Boundary, element techniques. Theory and applications in engineering, Springer Verlag, Berlin (1984) or Brebbia et al., Boundary Elements: An Introductory Course, McGraw-Hill, New York (1989)) can be employed.

Accordingly, a relationship between the epicardial (surface) potentials and the torso potentials can be expressed as the following linear matrix relationship:

$$V_T = A V_E \qquad (0)$$

where $V_E$ is the vector of epicardial potentials, $V_T$ is the vector of torso potentials, and A is the $N_T \times N_E$ of transfer matrix of influence coefficients between the heart (or epicardial envelope) and the torso (or electrode positions). The A matrix is thus based on the geometry and the conductivities of the media in the volume between the heart and torso. Although the torso can be understood to be homogeneous (i.e., uniform conductivity between the epicardial surface and the body surface), the A matrix can be modified to account for torso inhomogeneities (e.g., lungs, etc.). Accordingly, Equation (0) represents the forward problem of electrocardiography for computing body surface potentials from epicardial potentials.

One of ordinary skill can thus recognize that the A matrix is based on the geometrical relationship between the epicardial surface or envelope and the torso, and accordingly, the A matrix is based on node positions (corresponding to electrode positions) on the torso and node positions on the epicardium.

Figure 7A:
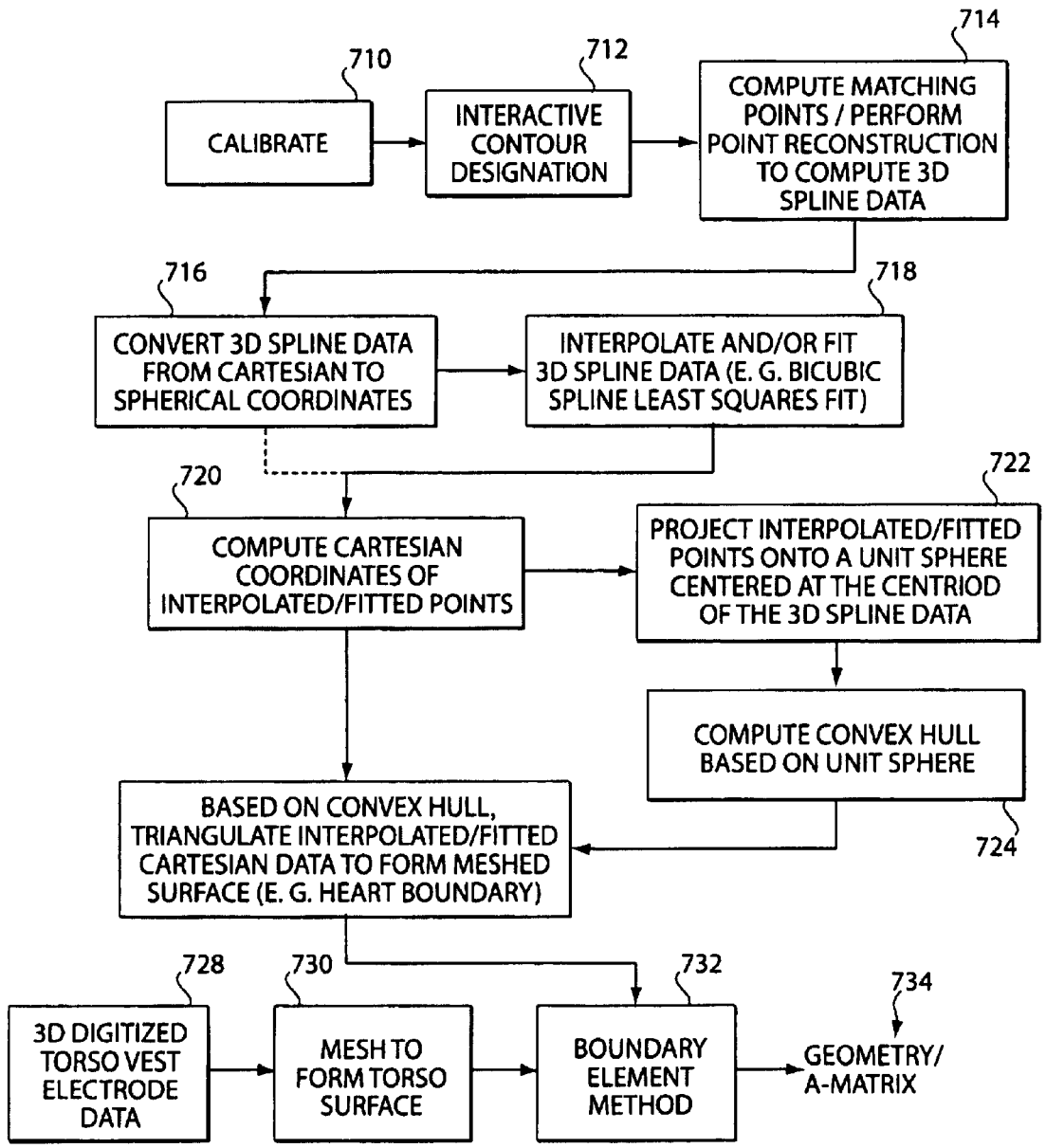
FIG. 7a illustrates one exemplary embodiment for modeling an epicardial surface based on two images.

The disclosed methods and systems can be employed to determine the values of the A matrix, where the disclosed methods and systems can employ projective geometry, epipolar geometry, point reconstruction, surface interpolation, and visualization techniques. FIG. 7A provides one block diagram for deriving such geometrical relationships based on biplane fluoroscopy, although those of ordinary skill will recognize that the disclosed methods and systems can be applied to other image data, including data acquired using a digital camera, for example.

In one embodiment, the disclosed methods and systems can include a calibration 710 that can be a single view calibration. Although the calibration procedure can be performed using various objects and/or procedures, in one exemplary process, the calibration procedure can include a calibration object and a planar board, where the calibration object and the planar board can be positioned to facilitate a calibration process such as the calibration process provided herein. For example, the calibration object and planar board can be configured with lead markers, and the calibration object and planar board can be composed of an X-ray transparent material such as acrylic, although other materials may be used. Further, an exemplary calibration object can be V-shaped and can include a number of markers, where in one embodiment, approximately twenty markers can be use. Similarly, a planar board can be used to include a number of markers, where in one embodiment, no less than approximately fifty markers may be included in the planar board. In some embodiments, where the object for which surface geometry is desired, is accessible, markers can be placed on the object. For the illustrated embodiments that include determining a surface geometry of an object such as a heart organ that may not be accessible, the aforementioned calibration objects (e.g, V-shaped, planar board) can be used.

In an illustrative V-shaped embodiment of a calibration object, such shape can provide that at least six non-coplanar markers can be detected or otherwise viewed from anterior lateral and oblique fluoroscopic views. As will be provided herein, views and/or detection of at least six non-coplanar lead markers can facilitate single view calibration.

Figure 7B:
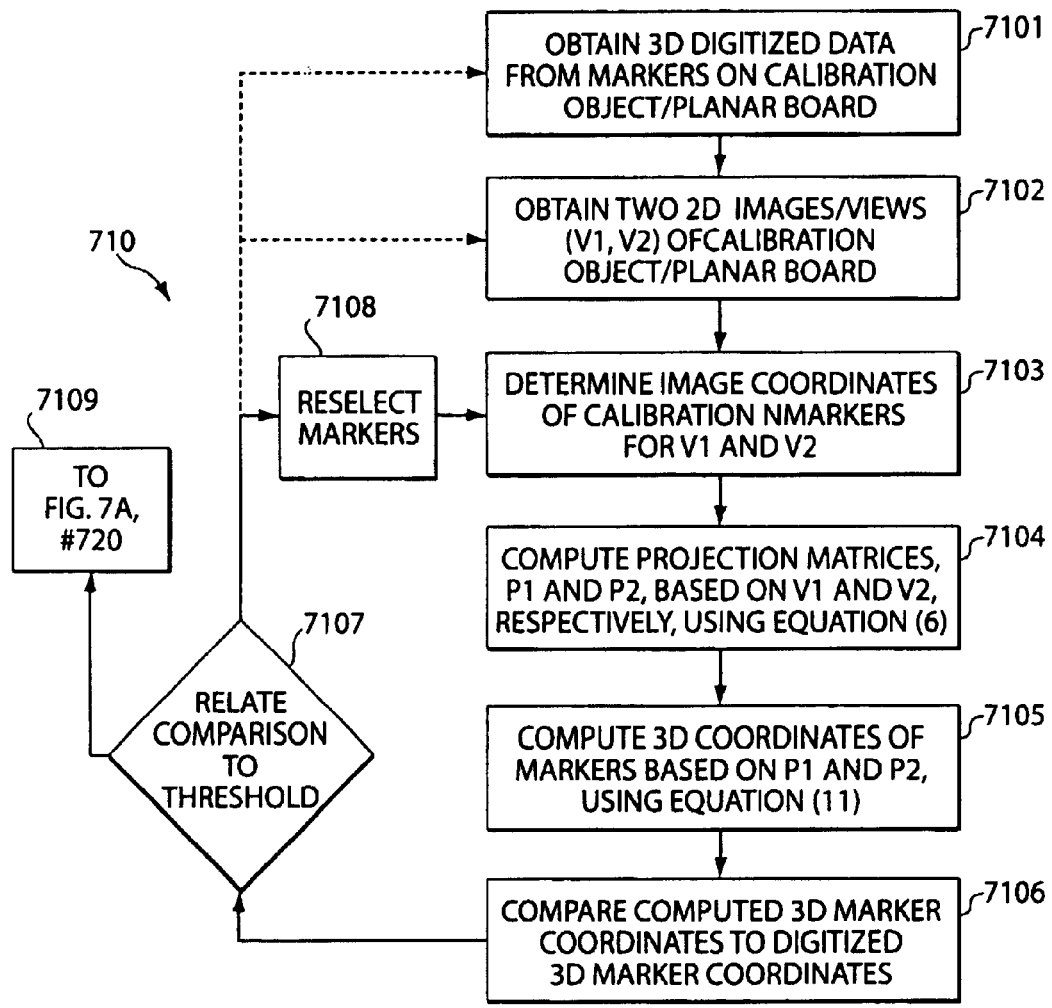

In one embodiment, and with reference to FIG. 7A 710, and one embodiment providing additional detail in FIG. 7B, a three dimensional (3D) digitizing instrument such as, for example, the Microscribe™ G2L system by Immersion Corporation, can be used to provide 3D data based on the relative positions of the markers on the calibration object, and similarly, on the planar board 7101. A subject can be presented in a supine position on a mattress, with the calibration object placed on or otherwise supported by and/or over the subject's torso, and the planar board can be positioned below the subject's back, including for example, under the mattress. Those of ordinary skill will recognize that such supine positioning is merely illustrative, and other positions can be used. With such aforementioned supine positioning, the 3D digitizing instrument can be employed to obtain 3D data indicating the relative positions of the calibration object and the planar board (e.g., the planar board can have markers that are accessible while placed under mattress, and other marker locations can be based on the accessible markers and previously obtained relative marker data.). Further, biplane fluoroscopy data acquired at, for example, a rate of thirty frames per second, can be acquired 7102 to enable data acquisition of at least six markers. The two fluoroscopic views may not and need not reveal the same calibration object markers.

It can be recognized that a camera or X-ray system such as a fluoroscopy system can be described by a central projection model known as the basic pinhole model, which provides a linear method to map "real-world coordinates" of an object, or a three-dimensional (3D) scene (e.g., the scene can include the subject having the calibration object and planar board positioned as provided herein), to two dimensional (2D) image coordinates. The mapping from real world, or "scene" coordinates, to image coordinates, can be via a projection matrix, P.

Figure 8:
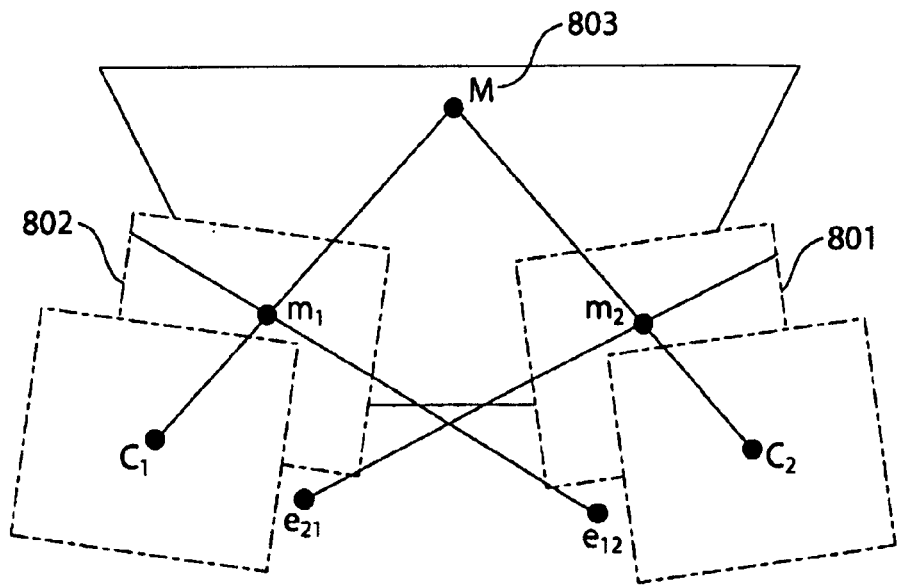
FIG. 8 presents an illustration of concepts related to the pinhole model.

FIG. 8 shows mappings from two 2D views 801, 802 to one 3D point 803, as will be provided herein; however, the concepts can also be understood relative to a single view (e.g., 801 or 802). With reference to either and/or both of the single image views 801, 802 of FIG. 8, the object space can be considered to be the 3D Euclidean space $R^3$, which can be understood to be embedded in the 3D projective space $P^3$. Additionally, the image space can be considered to be the 2D Euclidean space $R^2$, and can be understood to be embedded in the 2D projective space $P^2$. Accordingly, with reference to FIG. 8, a 3D point M 803 in the real world ("object space") can be projected through an optical center C1 (or C2) and onto a 2D point $m_1$ (or $m_2$) on a retinal plane using a linear transformation from $P^3$ to $P^2$, where such linear transformation can be effectuated by the projection matrix P.

The principal axis can be understood as the line through C1 (or C2) and perpendicular to the retinal plane which intersects the image plane at the projection of the camera/X-ray center, where such point is known as the principal point. Accordingly, a 3D Euclidean point $M=(x, y, Z)^T$ 803 can be mapped or otherwise transformed to a 2D image point $m_1$ (or $m_2$)$=(u=fx/z, v=fy/z)^T$, which one of ordinary skill will understand is not defined where z=0. This non-linear relationship between M 803 and $m_1$ (or $m_2$) can be linearly described using homogeneous coordinates for $m_1$ (or $m_2$) and M 803:

$$\begin{bmatrix} u \\ v \\ 1 \end{bmatrix} = \begin{bmatrix} f & 0 & 0 & 0 \\ 0 & f & 0 & 0 \\ 0 & 0 & 1 & 0 \end{bmatrix} \begin{bmatrix} x \\ y \\ z \\ 1 \end{bmatrix} \quad (1a)$$

where x, y, z, 1, and u, v, 1 are the projective and/or homogenous coordinates of real world or scene point M 803 and its respective image point $m_1$ (or $m_2$). Equation (1a) can also be rewritten in a form shown in Equation (1b):

$$sm=PM \quad (1b)$$

where $m=(u, v, 1)^T$ (e.g., $m_1$ or $m_2$) can represent the homogeneous coordinates vector of the image point m, $M=(x, y, z, 1)^T$ can represent the homogeneous coordinates vector of the object point M 803, s represents a scaling factor, and P is the aforementioned projection matrix describing the projection. In the aforementioned example, P is a 3×4 matrix.

Accordingly, Equations (1a) and (1b) represent a simplified expression for a projection matrix in a central projection where the camera/X-ray source coordinate system is aligned with the 3D world or scene coordinate system and the image points are referenced to the principal point. Because this alignment between the two images is generally not encountered, the projection matrix can be represented by the form:

$$P=KR[I|-t] \quad (2a)$$

where K represents the internal parameters of the camera/X-ray (focal length, principal point coordinates), and [R, t] represents external parameters (rotation and translation between the 3D scene and camera/X-ray coordinate systems). When applying Equation (2a) to Equation (1b), Equation (1b) can be expressed as:

$$sm=KR[I|-t]M \quad (2b)$$

Single view calibration techniques accordingly seek to determine a projection matrix P, given a set of points in a scene with known 3D coordinates (M, FIG. 8) and corresponding 2D image points ($m_1$ (or $m_2$), FIG. 8). For a given view 801, 802, for each point in the scene, $M_i$, and the corresponding image point $m_i$, Equation (2b) provides:

$$s_i m_i = P M_i \quad (3)$$

Expanding Equation (3) using homogeneous coordinates provides:

$$s \begin{bmatrix} u \\ v \\ 1 \end{bmatrix} = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix} \begin{bmatrix} x \\ y \\ z \\ 1 \end{bmatrix} \quad (4)$$

Expanding the matrix multiplication and substituting for s in the first two equations of Equation (4) provides:

$$(p_{31}x+p_{32}y+p_{33}z+p_{34}).u=p_{11}x+p_{12}y+p_{13}z+p_{14}$$

$$(p_{31}x+p_{32}y+p_{33}z+p_{34}).v=p_{21}x+p_{22}y+p_{23}z+p_{24} \quad (5)$$

When six or more points in the scene are provided, Equation (5) can be expressed as:

$$\begin{bmatrix} x & y & z & 1 & 0 & 0 & 0 & 0 & -ux & -uy & -uz & -u \\ 0 & 0 & 0 & 0 & x & y & z & 1 & -vx & -vy & -vz & -v \\ & & & & & \vdots & & & & & & \end{bmatrix} \begin{bmatrix} p_{11} \\ p_{12} \\ p_{13} \\ \vdots \\ p_{33} \\ p_{34} \end{bmatrix} = 0 \quad (6)$$

Accordingly, the projection vector ($p_{11}, p_{12}, \ldots, p_{34}$), and hence the projection matrix P, for a given view, can be determined through the eigenvalue decomposition of the Equation (6) matrix and selecting the eigenvector associated with the minimum eigenvalue.

Figure 9:
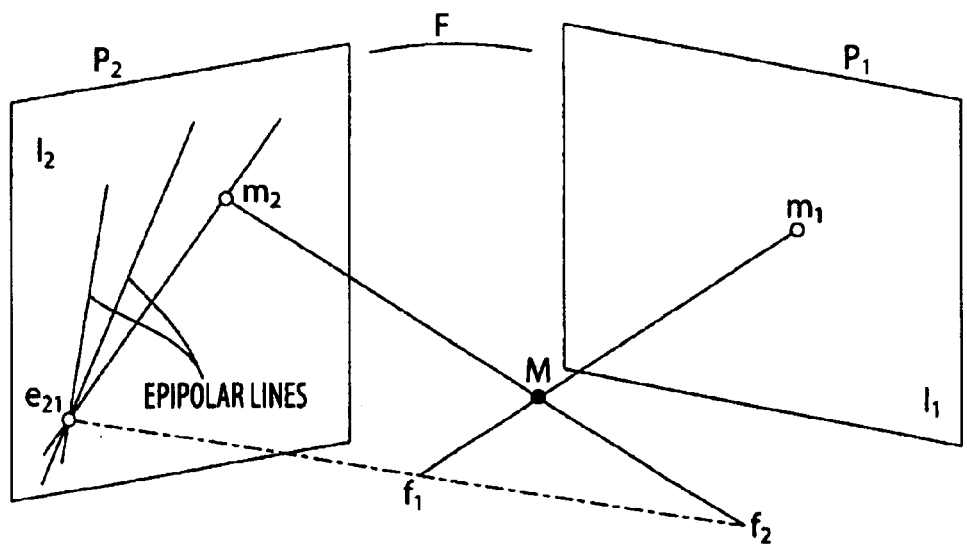
FIG. 9 also demonstrates concepts related to the pinhole model.

As those of ordinary skill in the art will recognize, and as provided in FIG. 8, in embodiments that employ biplane fluoroscopy and/or stereovision, the 3D scene can be imaged from two views simultaneously or sequentially (e.g., a moving camera around the scene). The geometry relating the two views can be described by an epipolar constraint that can be independent of the scene and can be based on the camera's/X-ray's intrinsic parameters and a relative relationship between the two fluoroscopic views. FIG. 9 accordingly represents the epipolar geometry of two fluoroscopic views described by projection matrices $P_1$ and $P_2$ respectively. With reference to FIG. 9, image points $m_1$ and $m_2$ can be referred to as corresponding image points as they represent the same scene object point M, in two different images (fluoroscopy views). These two points, $m_1$ and $m_2$, are constrained by the epipolar geometry, and as such, a given image point in the first view (e.g., $m_1$), corresponds to an epipolar line in the second view on which the corresponding image point (e.g., $m_2$) lies. Epipolar lines in the second view intersect at the epipole ($e_{21}$, FIG. 9) that corresponds to the image of the camera center/X-ray source for the first view ($f_1$, FIG. 9). Similarly, epipolar lines in the first view intersect at the epipole (not shown, FIG. 9) corresponding to the image of the camera center or X-ray source for the second view. The epipolar geometry can thus be represented by a 3×3 matrix that can be known as the fundamental matrix, F, which relates homogenous coordinates of corresponding image points from two views, such that:

$$m_1 = (u_1 v_1 1)^T$$

and, $$m2 = (u_2 v_2 1)^T$$

then, $$m_2^T F m_1 = 0 \qquad (7)$$

Accordingly, the fundamental matrix F can be determined from a set of corresponding image points (e.g., $m_1$, $m_2$), without prior knowledge of the scene or the projection matrices; however, when the projection matrices for the first and second matrices are known, F can be derived from the projection matrices and the epipole in the second view, $e_{21}$:

$$F = [e_{21}]_x P_1 P_2^+ \qquad (8)$$

where $P_1$ represents the projection matrix for the first view, $P_2^+$ represents the pseudo-inverse of the projection matrix for the second view, and $[e_{21}]_x$ represents the skew matrix formed from the epipole in the second image. The homogeneous coordinates of the epipole $e_{21}$ can accordingly be determined by solving equation $Fe_{21}=0$, and determining the eigenvector corresponding to the smallest eigenvalue of F.

Given Euclidean calibrated projection matrices $P_1$ and $P_2$ for the first and second views, respectively, and also given a pair of corresponding image points $m_1 = (u, v, 1)^T$ and $m_2 = (u', v', 1)^T$ of an object point $M = (x, y, z, t)^T$ in the scene, the 3D coordinates of point M can be recovered by triangulation. The following relationships can be applied to the first and second views:

$$s \begin{bmatrix} u \\ v \\ 1 \end{bmatrix} = \begin{bmatrix} p11 & p12 & p13 & p14 \\ p21 & p22 & p23 & p24 \\ p31 & p32 & p33 & p34 \end{bmatrix} \begin{bmatrix} x \\ y \\ z \\ t \end{bmatrix} \qquad (9)$$

-continued $$s' \begin{bmatrix} u \\ v \\ 1 \end{bmatrix} = \begin{bmatrix} p'11 & p'12 & p'13 & p'14 \\ p'21 & p'22 & p'23 & p'24 \\ p'31 & p'32 & p'33 & p'34 \end{bmatrix} \begin{bmatrix} x \\ y \\ z \\ t \end{bmatrix} \qquad (10)$$

It can be shown that, substituting for s and s', and combining equations (9) and (10) can provide:

$$[p_{11}\ p_{12}\ p_{13}\ p_{14}] \begin{bmatrix} x \\ y \\ z \\ t \end{bmatrix} - [p_{31}\ p_{32}\ p_{33}\ p_{34}] \begin{bmatrix} x \\ y \\ z \\ t \end{bmatrix} \cdot u = 0 \qquad (11)$$

$$[p_{21}\ p_{22}\ p_{23}\ p_{24}] \begin{bmatrix} x \\ y \\ z \\ t \end{bmatrix} - [p_{31}\ p_{32}\ p_{33}\ p_{34}] \begin{bmatrix} x \\ y \\ z \\ t \end{bmatrix} \cdot v = 0$$

$$[p'_{11}\ p'_{12}\ p'_{13}\ p'_{14}] \begin{bmatrix} x \\ y \\ z \\ t \end{bmatrix} - [p'_{31}\ p'_{32}\ p'_{33}\ p'_{34}] \begin{bmatrix} x \\ y \\ z \\ t \end{bmatrix} \cdot u' = 0$$

$$[p'_{21}\ p'_{22}\ p'_{23}\ p'_{24}] \begin{bmatrix} x \\ y \\ z \\ t \end{bmatrix} - [p'_{31}\ p'_{32}\ p'_{33}\ p'_{34}] \begin{bmatrix} x \\ y \\ z \\ t \end{bmatrix} \cdot v' = 0$$

and thus, $$\begin{bmatrix} P_1 - u \cdot P_3 \\ P_2 - v \cdot P_3 \\ P'_1 - u' \cdot P'_3 \\ P'_2 - v' \cdot P'_3 \end{bmatrix} \begin{bmatrix} x \\ y \\ z \\ t \end{bmatrix} = 0$$

where $P_1$, $P_2$, and $P_3$ represent the first, second, and third rows of the projection matrix $P_1$, respectively, and $P_1'$, $P_2'$, and $P_3'$ represent the first, second, and third rows of the projection matrix $P_2$. The coordinates of the point $M = (x, y, z, t)^T$ can be assigned to the eigenvector corresponding to the smallest eigenvalue of the matrix in Equation (11).

Accordingly, referring back to FIG. 7a, based on two images/views of the aforementioned calibration object and planar board scene (e.g., subject in supine position) that can be obtained through fluoroscopy, digital camera, or other imaging means 7102, image coordinates can be determined 7103 for at least six selected markers in the views, V1 and V2, where such markers can be on the calibration object and/or the planar board, and where such markers appear in both views. Using Equation (6) provided herein, respective projection matrices, $P_1$ and $P_2$, describing the internal matrices of the camera/X-ray or other imaging device, can be computed 7104 based on the image coordinates from the respective single views, V1 and V2. Equation (11), provided herein, can be employed to compute 3D coordinates for the corresponding markers 7105 based on the computed projection matrices ($P_1$, $P_2$). The markers for which the 3D coordinates are computed may include the six or more markers from which the projection matrices were computed, and/or other markers. It can thus be recognized that 3D coordinates can be computed for one or more markers, where, as provided herein, 3D computations for a comparatively greater number of markers may allow a comparatively better evaluation of the accuracy of the projection matrices. Accordingly, the computed 3D marker coordinates can be compared against the digitized 3D marker coordinates 7106, and such comparison can be further related to an accuracy criteria such as one or more thresholds 7107. Based on the threshold 7107, the calibration process may be deemed complete 7109, or may be performed again. For example, in one embodiment, statistics such as a mean error and/or standard deviation can be derived based on comparisons between computed 3D coordinates and digitized coordinates (e.g., for the various marker(s) for which 3D coordinates were computed), where such statistics and/or comparison can provide an accuracy measure of the projection matrices. In one embodiment, based on the statistics and/or the comparison, the calibration procedure can be re-performed based on a re-selection of markers 7108, where markers that may be considered better known may be re-selected, while those that may not be as well known may be avoided or otherwise de-selected. In an embodiment, re-performing calibration can include restarting from the obtaining of the 3D digitized data 7101, and/or the obtaining of the 2D images 7102. In one example, the aforementioned threshold can include five millimeters (e.g., difference between computed 3D coordinates and digitized coordinates), although such example is provided for illustration and not limitation.

Returning again to FIG. 7A, in one embodiment, a user can perform contour designation 712 by viewing multiframe animated images of the heart based on biplane fluoroscopic projections for the two views. The views can include the entirety of the object surface for which a geometry is desired, which in the illustrated embodiments, is the heart. Accordingly, a user can identify a frame for each view that can be associated with an outer boundary of the beating heart. For example, ECGI images can be obtained during cardiac activation, and therefore heart contours corresponding to end diastole can be identified, when a comparatively enlarged projection of the heart may be obtained. In some embodiments, a dye or other substance may be injected into the subject (human or otherwise) to facilitate identification of the outer boundary of the heart.

In one embodiment, a user or another can utilize a computer mouse or other designation scheme (joystick, stylus, etc.), to select, designate, determine, or otherwise delineate data points along an outer contour for each of the two views 712, where the selections can be made from a display of the two views. In some embodiments, a contour and/or boundary can additionally and/or optionally be automatically generated, determined, and/or detected using image processing techniques. Accordingly, a processor program associated with the displayed data can receive the user-provided contour data points and interpolate such user-designated data and/or otherwise process the data (e.g., automatic boundary/contour detection) to create a contour of the outer boundary. In one embodiment, the user or another can specify a number of points to include in the contour. For example, a user may provide that one-hundred points be included in the contour. In an embodiment such as provided by FIGS. 10a and 10b, the heart contour created by the processor program, based on the user-delineated points, can be visually displayed (e.g., 1004) such that the contour may be superimposed upon the displayed image data.

Referring now to FIGS. 10a and 10b that provide two identified views (e.g., images) using biplanar fluoroscopy, as provided herein previously, a point $m=(u, v, 1)^T$ 1002 on the heart contour 1004 can define an epipolar line 1006 in the second view, where the epipolar line can be expressed as $l=Fm^T$, where F is the fundamental matrix F relating the two views as derived from the projection matrices $P_1$ and $P_2$ and based further on Equation (8). The intersection of the epipolar line l 1006 with the heart contour in the second image/view 1008 can be associated with the corresponding (matching) contour point, m' 1010. Similarly, m' defines an epipolar line in the first view (not shown) that can be expressed as $l'=F^Tm'$.

For example, a point $m_1$ (e.g., image coordinate) can be selected, where $m_1$ can be on or otherwise associated with the designated contour in the first view. Based on the fundamental matrix (e.g., the projection matrices), a first epipolar line can be computed as provided herein, and also determined can be the intersection of the first epipolar line with the contour in the second view. Such intersection can provide two matching contour points in the second view, both of which can be associated with a second epipolar line. Accordingly, based on either one of the two matching points from the second view and the fundamental matrix, the second epipolar line can be computed, and the intersection of the second epipolar line with the first view/image can be determined to identify $m_1$ and a second point along the designated contour in the first view. Those of ordinary skill will recognize that based on the point $m_1$, three additional points can be computed (e.g., two matching point pairs), and such computations can be computed for a number of points along the designated contour in the first view. It may be understood that the designations of first view and second view as described herein are merely arbitrary, and the disclosed methods and systems could identify matching points based initially on points derived from a designated contour in the second view.

Returning again to FIGS. 10a and 10b, also shown is a frontier point (i.e., intersection of two contour generators) 1012, and the corresponding epipolar line 1014 which is tangent to the heart contour.

Accordingly, returning again to FIG. 7A, for a designated or otherwise selected (e.g., via a user or another) number of data points along the aforementioned selected and/or designated contour, matching points as provided herein can be computed, and for a pair of matching contour points (e.g., m=(u, v) 1002, m'=(u', v') 1010, FIGS. 10a, 10b), point reconstruction can be performed to determine or otherwise reconstruct 3D coordinates (e.g., M=(x, y, z)) corresponding to the object or real world point based on the projection matrices and Equation (11) 714.

Figure 11:
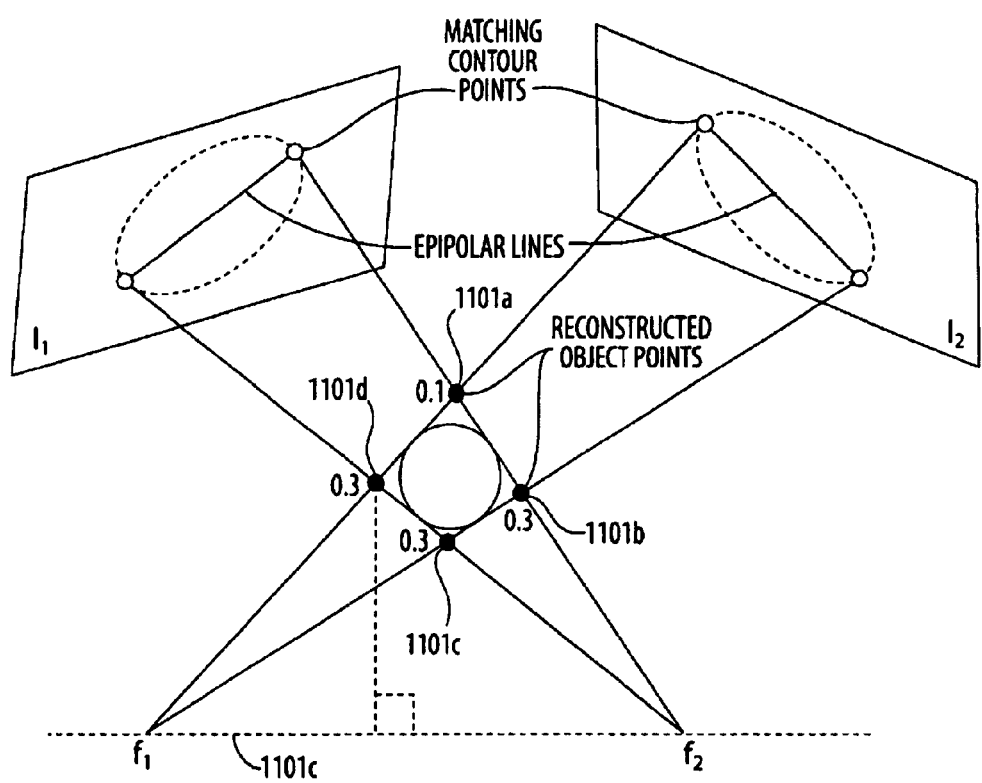
FIG. 11 displays four object points reconstructed using point reconstruction and illustrative weights.

As FIG. 11 indicates, four points and/or sets of 3D coordinates 1101a–d can be reconstructed from a pair of matching contour points, although those of ordinary skill will recognize that a pair of matching and/or corresponding frontier points reconstructs a single object point.

Referring again to FIG. 11, focal point $f_1$ for the first view (FIG. 10a) can be determined by solving the homogeneous equation $P_1f_1=0$, while focal point $f_2$ can be similarly determined for the second view (FIG. 10b). As FIG. 11 indicates, focal points $f_1$ and $f_2$ can define a line 1102, and the reconstructed points can be weighted based on a distance of the reconstructed 3D points 1101a–d from the line 1102. In the illustrated example, a reconstructed point associated with a comparatively greatest distance 1101a can be assigned a weight of 0.1, while the other reconstructed points 1101b–d can be assigned weights of 0.3. Those of ordinary skill in the art will recognize that such weight assignments are merely illustrative of one weighting scheme, and other weighting schemes (e.g., uniform weights, weights inversely proportional to the distance from the centroid, etc.) can be used without limiting the scope of the disclosed methods and systems.

Referring to FIG. 7A and FIG. 11, the four weighted 3D points 1101a–d thus can be understood to approximate a b-spline 714, where the point 1101a farthest from line 1102 may have the smallest effect on the shape of the b-spline, whereas the three points 1101*b–d* closer to the line 1102 can have a comparatively greater influence.

The matching of contour points, point reconstruction, and b-spline approximation 714 can be repeated for a specified number of points along the contour (e.g., one-hundred) to provide a set (e.g., one-hundred) of 3D b-splines. Referring again to FIG. 7A, the 3D spline data can be converted to spherical coordinates 716, and in some embodiments, can optionally be interpolated and/or fitted to a surface 718, where in one embodiment, the fit can be based on a bicubic spline least squares fit. As FIG. 7A also indicates, the fitted/interpolated data can be converted to or otherwise projected to Cartesian coordinates 720. Further, the fitted/interpolated data can be projected onto a unit sphere 722, where the unit sphere has a center based on the centroid of the 3D b-spline data. The Cartesian data can be combined 726 with connectivity information based on a convex hull of the aforementioned unit sphere 724, to triangulate the Cartesian data based on the connectivity information to form a meshed surface that approximates the heart boundary 726.

Those of ordinary skill will recognize variations in the illustrated methods and systems, which can include, for example, systems and methods that may not generate b-splines, but may cluster the 3D data (four reconstructed points from matching pairs of contour points) and may compute a volume that can be fitted to a surface. In a variation of the methods and systems, those of ordinary skill will recognize that connectivity data can be extracted without projecting data to a unit sphere and computing a convex hull.

As FIG. 7A also indicates, 3D digitized data from the torso-vest electrode positions (x, y, z coordinates) 728 can be meshed to form the torso surface 730 associated with the torso geometry. Those of ordinary skill in the art will recognize that the meshing of the torso vest electrodes 730 can be performed as outlined previously with respect to the outer boundary of the heart. Accordingly, the torso nodes, or vest electrode positions, can be projected onto a unit sphere centered at the centroid of the torso nodes, a convex hull can be computed, and using connectivity information from the convex hull, the torso nodes can be meshed. In some embodiments, conversion to spherical coordinates, fitting, and/or interpolation can optionally be performed.

The meshed surfaces of the torso 730 and the heart 726 can be associated (e.g., registered) and provided to a boundary element method module 732 which can compute the relationships between the meshed surfaces and thus provide the geometry or A-matrix 734 provided in Equation (0).

The disclosed methods and systems for determining heart geometry were applied to a realistic plastic heart model that was imaged using biplane fluoroscopy at various dual angles: Anterior Posterior (AP) 0°, Left Anterior Oblique (LAO) 70°; Right Anterior Oblique (RAO) 10°, LAO 70°; RAO 20°, LAO 70°; RAO 30°, LAO 60°; RAO 40°, LAO 50°; RAO 50°, LAO 40°. The heart was reconstructed from each pair of biplane angles. Additionally, the phantom heart geometry was acquired using a CT scanner at a sampling interval of 3.2 mm and a pitch of 0.5. The heart boundary in each CT slice was segmented using deformable model segmentation. The segmented cross sectional contours were then meshed and the resulting surface used as gold standard for validation of the fluoroscopy-reconstructed heart.

As provided herein, accurate localization of the recording electrodes on the body surface can be crucial for increased accuracy, and a mannequin with ninety two visible markers (simulating actual electrodes) on the anterior surface was employed. A V-shaped calibration object was placed over the mannequin. Eight markers on the calibration object and six markers on the mannequin were digitized using a mechanical digitizer (e.g., MicroScribe™ G2L, Immersion Corporation) and used for single camera calibration of each picture in stereo photographs. A total of three pairs of stereoscopic photographs were taken with a digital camera (SONY™ DSC-S85). Taken in pairs, the photographs were calibrated and the 3D coordinates of corresponding markers were determined using point reconstruction as provided herein relative to FIG. 7. These were compared to the actual coordinates digitized using the mechanical digitizer (MicroScribe™ G2L, Immersion Corporation).

The fluoroscopy based algorithm for reconstructing the heart geometry was validated in a human subject. The subject's heart was imaged using biplane fluoroscopy (RAO 40°, LAO 50°), with the subject in a supine position while the marker board was situated under the subject with the calibration object supported by/over the torso/chest. The markers were digitized using a mechanical digitizer (e.g., MicroScribe™ G2L, Immersion Corporation) and used to calibrate the fluoroscopic views. Because of the low quality of the fluoroscopic images, the manually segmented heart contour was enlarged by 10% to ensure that the reconstructed envelope surrounded the heart surface. The fluoroscopy-reconstructed heart was validated in comparison with the CT heart imaged using ECG-gated axial CT scanning (Phillips, Mx8000) at a resolution of 0.6 mm and a pitch of 1.

Signed (positive implies outside; negative implies inside) distance measure quantified the differences between the fluoroscopy-reconstructed heart and the gold standard CT heart. The distance error was computed as follows:

For each node, $N_r$, on the fluoroscopy-reconstructed heart,

Compute the 3D Euclidean distance to each node on the gold standard CT heart.

Select the minimum Euclidean distance as the error, $E_r$, associated with node $N_r$.

Denote the nearest node to $N_r$ on the gold standard CT heart by $NN_g$

Compute the dot product between the vector joining the centroid of the gold standard CT heart and $NN_g$ with the vector joining $NN_g$ and $N_r$.

Assign the sign of the dot product to the error measure, $E_r$.

Mean, maximum, minimum and standard deviation of the signed distance errors over the entire surface of the fluoroscopy-reconstructed hearts, are computed.

Noninvasive Electrocardiographic Imaging (ECGI) was performed in a human subject during normal heart rhythm. Body surface potentials were acquired from 224 ECG electrodes using a previously described mapping system and an electrode vest. (See, for example, Rudy Y, Burnes J E. Noninvasive electrocardiographic imaging. *Annals of Noninvasive Electrocardiology.* 1999; 4:340–59., incorporated herein by reference in its entirety). Recorded electrocardiograms were amplified and band pass filtered between 0.5 and 500 Hz. The heart was imaged using CT and biplane fluoroscopy. The fluoroscopy based method and system was employed to reconstruct an envelope around the subject's heart. The heart geometry was also computed based on the CT slices. The locations of the body surface electrodes were digitized using a 3D mechanical digitizer (e.g., MicroScribe™ G2L, Immersion Corporation). Consequently, two data sets described the subject's geometry: (1) CT constructed heart with digitized body surface electrodes; and, (2) Fluoroscopy reconstructed heart envelope with digitized body surface electrodes. Using a boundary element method, the transfer matrices relating epicardial (for CT) or heart envelope (for fluoroscopy) to body surface potentials was derived.

The recorded body surface potentials were employed to compute potentials on the CT-constructed epicardium and the fluoroscopy-reconstructed envelope during normal cardiac electrical activation. Imaged potentials on these two surfaces were compared to evaluate the accuracy of the ECGI/fluoroscopy approach relative to the ECGI/CT approach.

Figure 12:
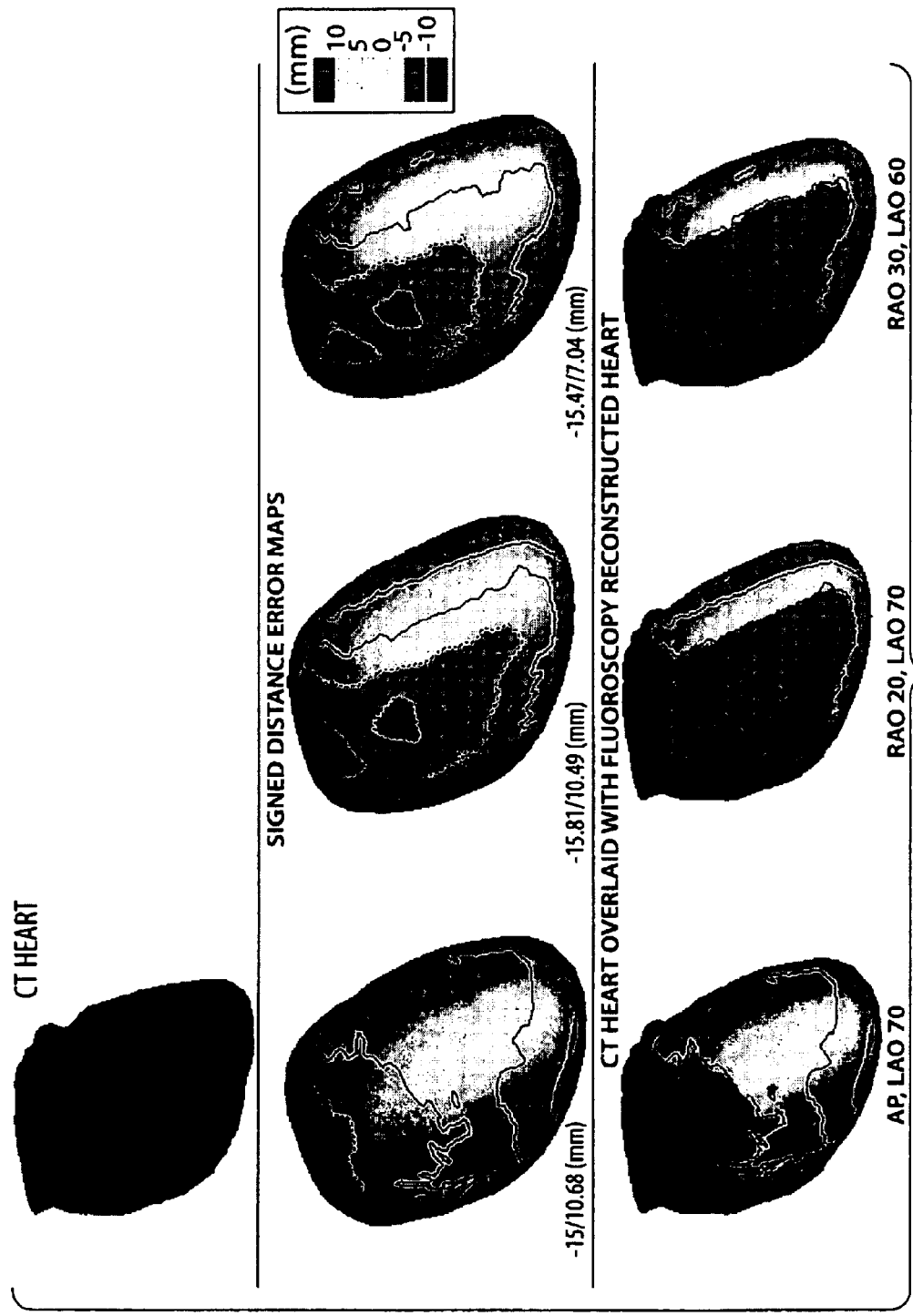
FIG. 12 includes a reconstructed phantom heart from two fluoroscopic views; a CT heart (top) is shown for reference; signed distance error maps (middle row) are shown for AP, LAO 70° (left column); RAO 20°, LAO 70° (second column) and RAO 30°, LAO 60° (right column); maximum negative and maximum positive distance error values are displayed; CT heart overlaid with the distance error map is also shown (bottom row).

Table 1 summarizes the results for the fluoroscopy-reconstructed phantom heart. For pairs of biplane angles, minimum, maximum, mean, and standard deviation of the absolute distance errors relative to the CT heart were computed. In all cases, the mean distance error is approximately 4 mm. FIG. 12 provides results for selected biplane angles; AP, LAO 70° (left column); RAO 20°, LAO 70° (middle column); and RAO 30°, LAO 60° (right column). The reference CT heart as segmented and constructed from the CT slices is shown in the top left panel. The middle row shows the fluoroscopy-reconstructed heart with signed distance error maps. Negative values indicate that the region of the fluoroscopy-reconstructed heart is interior to the CT heart and positive values indicate that it is exterior. The last row overlays the CT heart on the signed distance error map.

In addition to biplane fluoroscopy, the disclosed methods and systems for determining the heart geometry can be extended to multiple plane fluoroscopy. FIG. 13 shows the fluoroscopy-reconstructed heart from four views (AP, LAO 70° and RAO 30°, LAO 60°) in comparison to CT. Two sets of 3D splines are reconstructed from pairs of biplane angles and the convex hull of the splines is obtained and meshed. Comparatively improved distance errors (mean decreased to 3.8 mm) suggest that incorporation of four views can improve the reconstructed heart geometry. The last row of Table 1 summarizes the results for the four views case.

In one embodiment, point reconstruction techniques were employed to reconstruct the electrode positions from stereo photographs (FIG. 14A). The electrode markers ('x') affixed on the anterior surface of a mannequin were identified in the images and matched. The projection matrices were obtained for the respective photographs using single view camera calibration as provided previously herein. The reconstructed electrode positions were compared to the actual digitized coordinates from the scene. FIG. 14B shows the signed distance error map for the reconstructed electrodes on the anterior surface of the mannequin. The mean absolute distance error was 1 mm.

Figure 15:
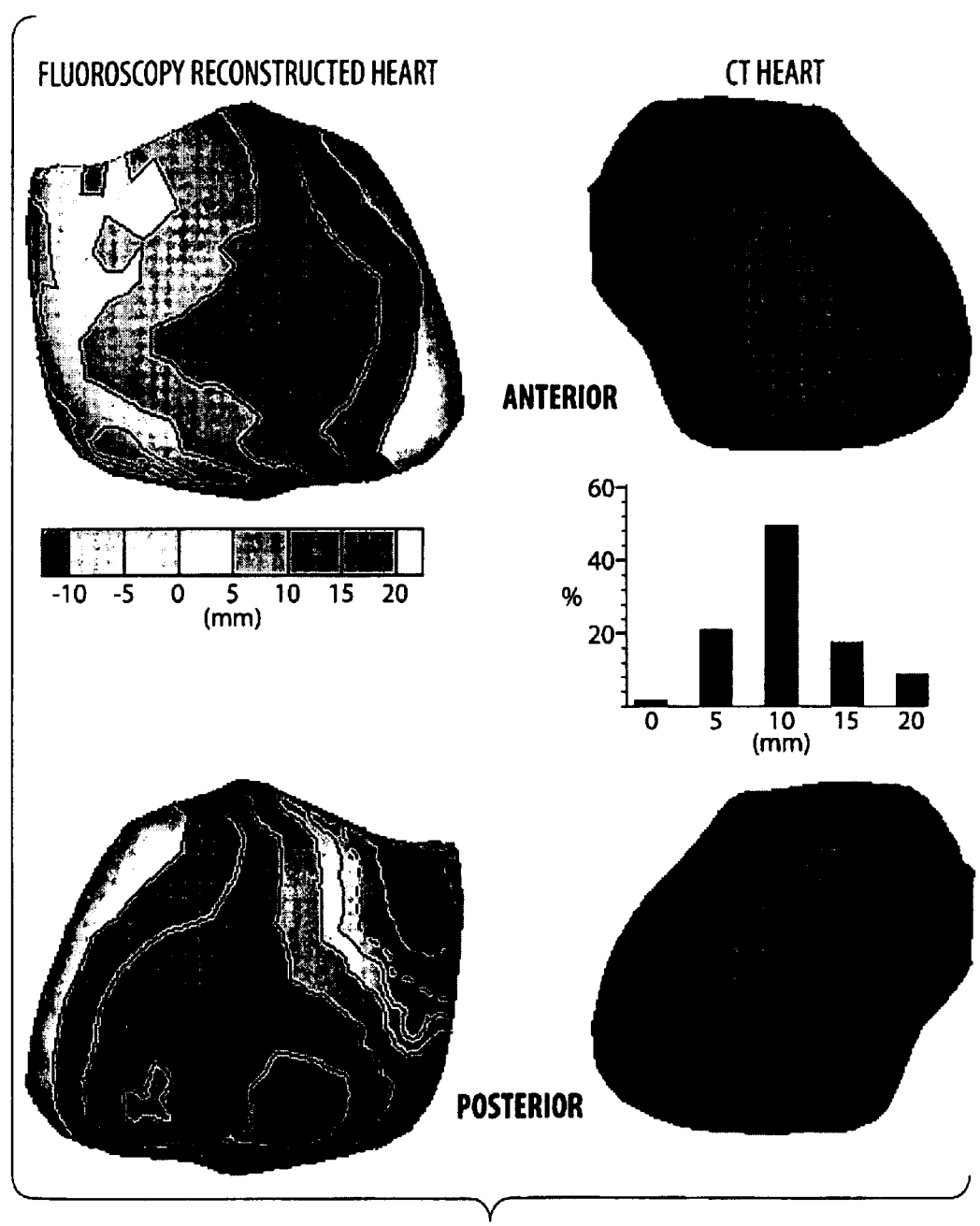
FIG. 15 left panel, includes signed distance error maps for anterior (top) and posterior (bottom) views of a reconstructed heart of a human subject; a CT heart (Right Panel) is also shown; an inset provides a histogram of nodes on the fluoroscopy reconstructed heart versus absolute distance (0, 5, 10, 15, 20 mm) from the CT heart.

FIG. 15, left column, shows the signed distance error map for the fluoroscopy-reconstructed epicardial envelope in a human subject. The CT heart (right column) was used as gold standard for comparison. Anterior (top row) and posterior (bottom row) are shown. Positive values indicate that the fluoroscopy-reconstructed surface is exterior to the CT heart surface, while negative values indicate that it is interior. The average absolute distance error was 10 mm. The inset shows the histogram of nodes on the fluoroscopy reconstructed epicardial envelope at 0, 5, 10, 15 and 20 mm absolute distance from the CT heart. More than 70% of the nodes on the fluoroscopy reconstructed envelope are within 10 mm distance from the CT heart.

Figure 16:
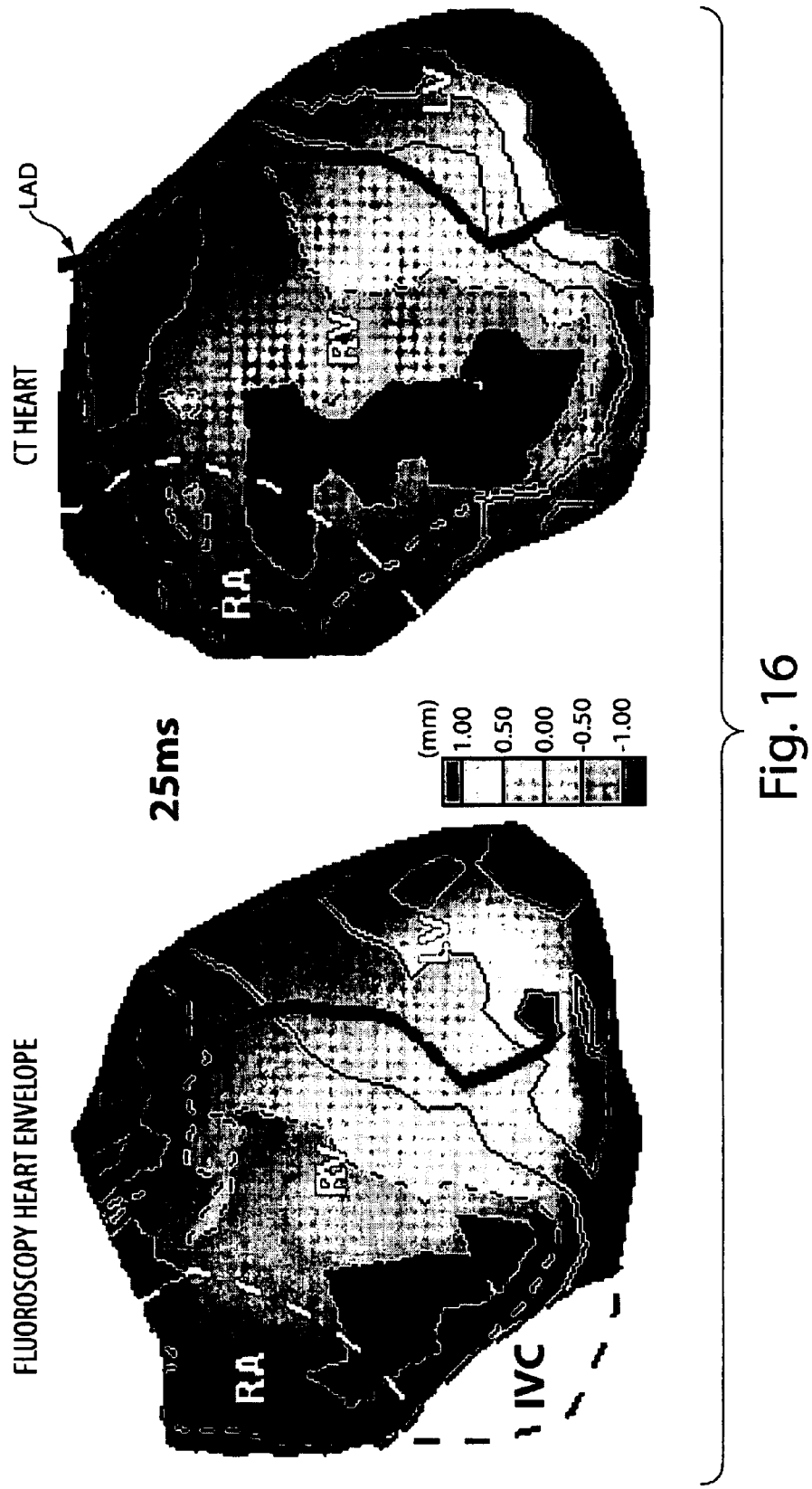
FIG. 16 includes a non-invasively imaged epicardial potential map in a human subject using the fluoroscopy-reconstructed heart (left) and CT heart (right.). An image is obtained 25 ms after QRS onset. RA, right atrium; RV, right ventricle; LV, left ventricle.

FIG. 16 shows epicardial potentials imaged noninvasively using the fluoroscopy-reconstructed epicardial envelope (left image) and using the CT heart (right image) at 25 ms following the onset of ventricular excitation (QRS onset). The potential minimum associated with right ventricular (RV) breakthrough (arrival of activation front to the RV epicardial surface) is reconstructed in both hearts, although with reduced amplitude in the fluoroscopy-reconstructed image. In addition, the overall potential patterns in both hearts reveal a global potential gradient from base to apex (negative potentials in green to positive potentials in red). The correlation coefficient (a measure of pattern similarity) between the potentials on the fluoroscopy reconstructed envelope and the nearest points on the CT heart is CC=0.70.

Accordingly, returning to Equation (0), which is based on the aforementioned A matrix that provides the geometrical relationship between the torso and the epicardial surface of the heart, Equation (0) can be rearranged to express the epicardial potentials in terms of the body surface potentials and the inverse of the A matrix:

$$V_E = A^{-1} V_T \quad (12)$$

The problem of determining the inverse of the A matrix is ill-posed as small perturbations in the data (e.g., measurement noise or geometrical errors) can cause large unbounded errors, which accordingly can require regularization of the solution to Equation (12). In one embodiment, Tikhonov regularization (See, Tikhonov A N, Arsenin V Y, "Solutions of ill-posed problems," (trans from Russian) Wiley, NY (1977), or Tikhonov et al., "Solutions of ill posed problems," 27–94, VH Winston & Sons, Washington D.C. (1977) which are hereby incorporated herein by reference) can be used to stabilize the solution to Equation (12) by imposing constraints on the magnitudes or derivatives of the computed epicardial potentials, which includes determining an epicardial solution, $V_E$, that minimizes the following objective function:

$$\text{Minimize over } V_E (\|AV_E - V_T\|^2 + t\|LV_E\|^2) \quad (13)$$

The first term in Equation (13) represents the least-square solution of Equation (12), while the second term in Equation (13) is a regularization term that imposes bounds on the amplitude of the solution to Equation (12). Those of ordinary skill recognize that the regularization parameter, t, controls the degree of the imposed constraint and provides a balance between the accuracy and stability of the solution, while L is a regularization operator (e.g., unity, gradient, or Laplacian). In one example, the regularization parameter, t, can be determined using the CRESO (Composite Residual and Smoothing Operator) method. (See, for example, Colli Franzone P, Guerri L, Tentoni S, Viganotti C, Baruffi S, Spaggiari S, Taccardi B, "Mathematical procedure for solving the inverse problem of electrocardiography," Math Biosci, 77:353–96 (1985), and Colli-Franzone et al., "Finite element approximation of regularized solutions of the inverse problem of electrocardiography and applications to experimental data" Calcolo, 1985, 22:91–186, which are incorporated herein by reference) and has been found to perform comparably to the "optimal" t that provides the minimum RMS error between the computed $V_E$ and the measured $V_E$ (e.g., experimental studies). See, Messinger Rapport B J, Rudy Y, "Computational issues of importance to the inverse recovery of epicardial potentials in a realistic heart-torso geometry" (published erratum appears in Match Biosci 1990 April; 99(1):141], Math Biosci, 97:85–120 (1989), which is incorporated herein by reference. The CRESO regularization parameter, t, depends on the vector $V_T$ and the matrix A. Accordingly, computing the epicardial potentials, $V_E$, is based on non-invasively obtained data that includes the torso surface electric potentials, $V_T$, (e.g., torso vest electrode data) and geometry data (e.g., CT, bi-plane X-ray, etc., to develop the A matrix).

As provided herein, Tikhonov regularization imposes constraints on the magnitudes or derivatives of the computed epicardial potentials to provide a solution. Applying these constraints requires some a-priori knowledge of the solutions' properties, which, in the illustrated embodiments, can cause a spatial smoothing of epicardial potentials that may reduce spatial resolution and diagnostically meaningful data or information. The Tikhonov regularization also requires an accurate determination of the aforementioned regularization parameter, t, which determines the constraint level. The aforementioned methods to determine the regularization parameter (e.g., Composite Residual and Smoothing operator (CRESO), L-curve, and Zero crossing) may not perform consistently and can be sensitive to the noise-level of the data. In some cases, a-priori information and manual adjustment may be required to choose an optimal regularization parameter. For example, a-priori knowledge of the number of ectopic foci (sites from which excitation is initiated) may influence the level of regularization applied.

A complementary approach to solving Equation (12) includes the Generalized Minimal Residual (GMRes) method which, unlike the Tikhonov regularization, is not based on imposing constraints and therefore does not include a-priori data or information about the solution or determination of a regularization parameter. Referring again to Equation (12), GMRes is thus an iterative method of computing $V_E$ from $V_T$ without imposing constraints on the solution.

As in known in the art, the GMRes method belongs to the class of Krylov subspace iterative methods. Generally, for the linear problem Ax=b, where A is a matrix and x is a vector (see, e.g., Equation (0)), the Krylov space of A is the subspace spanned by x, Ax, $A^2$x, etc. Accordingly, if M is a preconditioner, such that $M^{-1}$ A≈I (identity matrix), then for $M^{-1}$ (Ax−b)≈e, as e approaches zero, $M^{-1}$ approaches an approximation of $A^{-1}$. Hence, an iteration can be constructed as $x^{k+1}=x^k+M^{-1}(Ax^k-b)$, where the error at an iteration k can be expressed as $M^{-1}(Ax^k-b)$. Those of ordinary skill will recognize that GMRes is one approach for reducing the error to provide an approximation for $M^{-1}$ (i.e., $A^{-1}$) which uses an orthogonal Arnoldi decomposition of the A matrix.

Accordingly, with specific reference to Equations (0) and (12), given a vector $V_T$ and the matrix A, an n-dimensional Krylov subspace K(n) can be based on a set of linear combinations of the vectors $V_T$, $AV_T$, $A^2V_T$, ..., $A^{n-1}V_T$. At the $n^{th}$ GMRes iteration, the A matrix inverse can be approximated by a projection of A, $p_n(A)$, onto K(n). Accordingly, based on Equation (12), epicardial potentials, $V_E$, can be approximated by $p_n(A)V_T$.

The GMRes method proceeds by constructing, at the nth iteration, an orthonormal basis for the Krylov subspace, K(n). Because the A matrix is generally non-square (e.g., number of torso electrodes is generally not equal to number of reconstruction points on the epicardium), the disclosed methods and systems can be understood to include multiplying both sides of Equation (0) by $V_T$ and applying a GMRes method to the solution of $A^TAV_E=A^TV_T$ ($A^TA$ is a square matrix). Since the Krylov subspaces form a nested sequence, the norm of the residual error, $\|AV_E-V_T\|$, decreases as n increases. A solution with reduced contamination from noise components can be achieved by stopping the iterations of the GMRes method.

As provided herein, at the $n^{th}$ GMRes iteration, the matrix $A^{-1}$ can be approximated by the projection of A, p(A), onto the Krylov subspace, K(n). It is understood in the art that such projection subspace, K(n), can be represented as an upper triangular Hessenberg matrix, H(n). Further, the number of iterations (e.g., the value of n) can be based on the observation that, as n increases, the condition number of H(n) increases (i.e., H(n) can become ill-conditioned) while the norm of the residual error, $\|AV_E-V_T\|$, decreases. A plot of the condition number of H(n) versus the norm of the nth residual error illustrates the effect of GMRes iterations on these two quantities, and is shown as FIG. 7.

Figure 17:
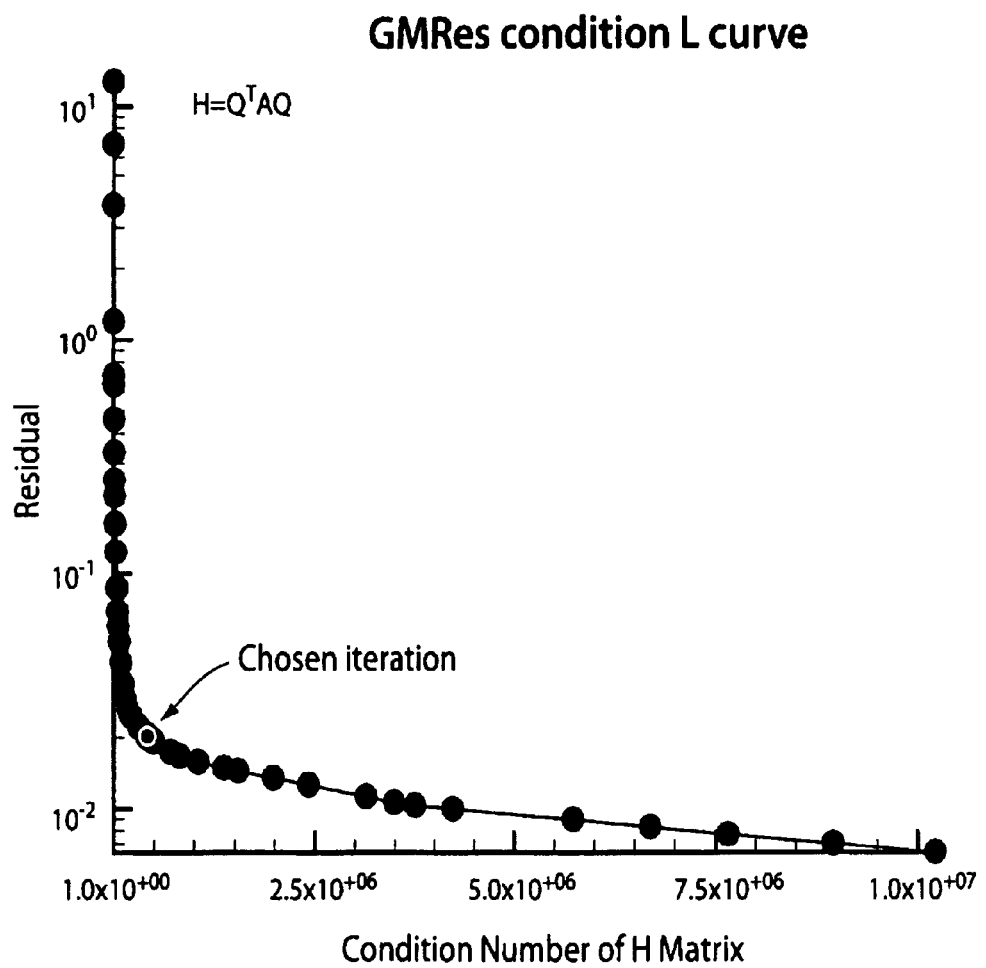
FIG. 17 represents a condition L curve.

As FIG. 17 indicates, for a method and system that utilize GMRes to compute a solution to Equation (12) and hence can be based on a number of iterations, as the iteration number increases, the condition of an associated Hessenberg matrix can be accompanied by a decrease in the norm of the residual error, $\|AV_E-V_T\|$. As FIG. 17 indicates, this decrease can be comparatively significant during the first iterations when compared to subsequent iterations. Accordingly, one of skill in the art will recognize that the incremental decrease in residual error, $\|AV_E-V_T\|$, for additional iterations, may be insignificant after a given number of iterations, while the condition number of the Hessenberg matrix continues to increase.

Based on FIG. 17, one compromise between number of iterations, decreased residual error, and Hessenberg matrix condition can include selecting a number of iterations for the GMRes method that is associated with or otherwise based upon a representation of residual error versus condition number, and where such number of iterations can be a compromise between residual error decrease and condition number increase. For the FIG. 17 embodiment, for example, a selected or chosen number of iterations can be associated with the "elbow" of a curve that represents residual error (norm) based on condition number of the Hessenberg matrix. Those of ordinary skill will recognize FIG. 17 to represent a "condition L curve," which has a corner that can otherwise be understood to be an elbow. In one embodiment, a corner of a condition L curve can be selected by a curvature detection module that computes curvature along a condition L curve. In one example, a selected number of iterations can be a number of iterations associated with a comparative maximum curvature of a condition L curve. In an embodiment, a selected number of iterations can be determined from a corner of a "L curve" (compare to "condition L curve") that can plot or otherwise represent residual error (norm) and (e.g., versus) solution norm. Accordingly, in such an embodiment, a number of iterations can be based on the corner of a L curve, which can be based on a comparative maximum curvature, although other methods can be used.

In some embodiments, a selected number of GMRes iterations can be determined based on an increase in spatial frequency of a reconstructed potential map, where such evaluation can be performed after an iteration of the GMRes technique, and can be based on a Fourier transform or other frequency representation of a potential map. Further, a selected number of GMRes iterations can be based on comparative amplitudes of a solution norm that is computed at an iteration, where a comparatively increased amplitude in a solution norm at a selected iteration can be a basis for selecting an iteration number. The aforementioned four techniques for selecting a GMRes iteration number are shown in FIG. 18 818, and those of ordinary skill in the art will recognize that other techniques can be used.

Figure 18:
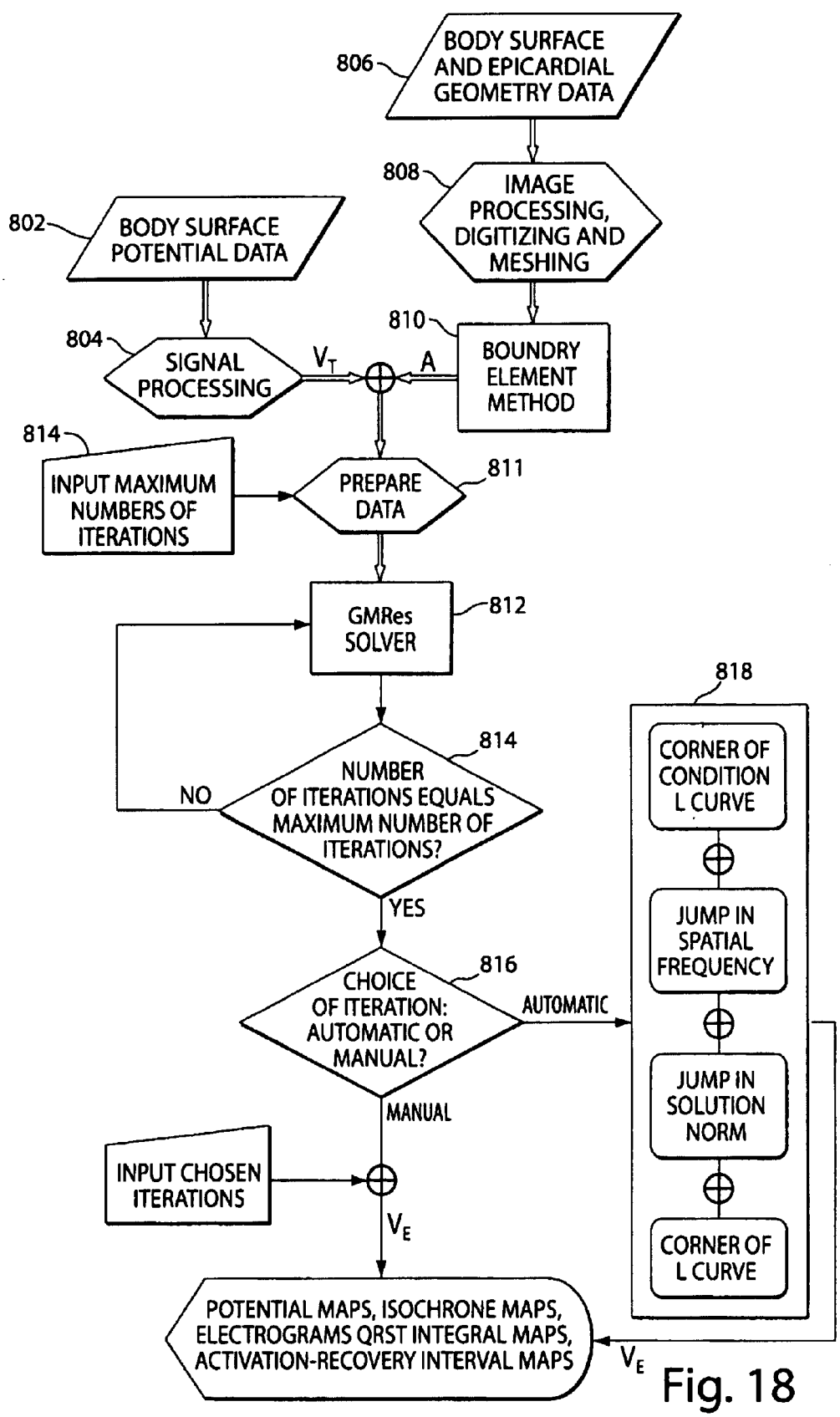
FIG. 18 is a block diagram for determining epicardial potentials using a GMRes module.
Figure 19A:
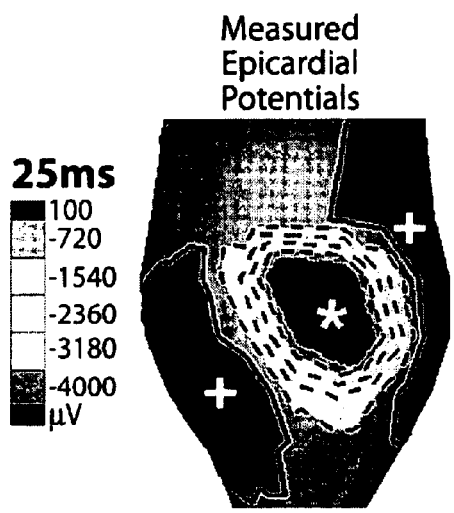
FIGS. 19a, 19b, and 19c present epicardial potential maps for pacing from a single anterior ventricular site, 25 milliseconds after a pacing stimulus, as measured, and as reconstructed using GMRes and Tikhonov reconstructions, respectively.
Figure 19B:
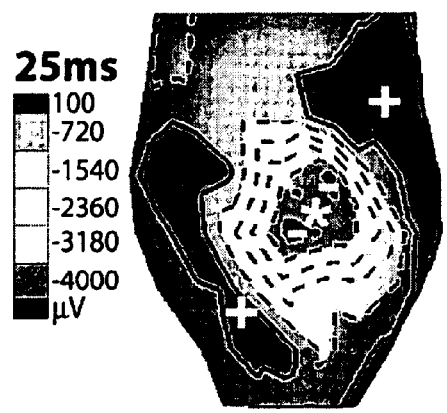
Figure 19C:
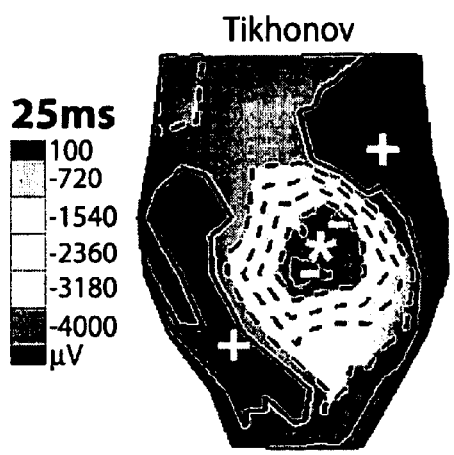
Figure 19D:
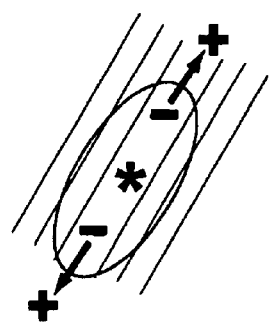
Figures 1, 20A:
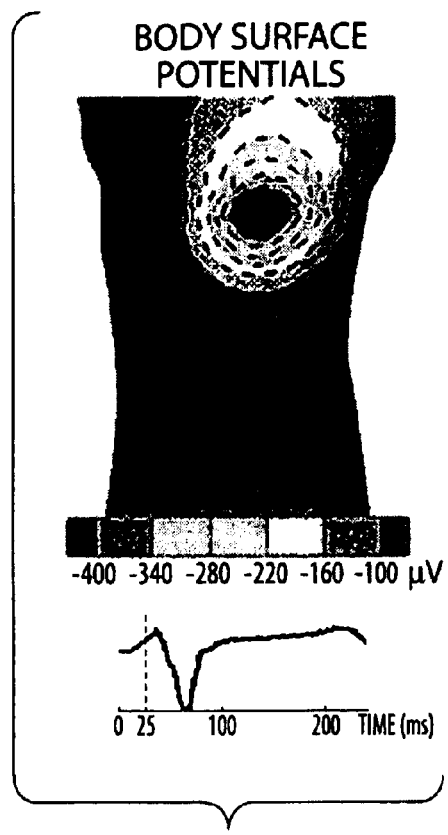
Figures 2, 20A:
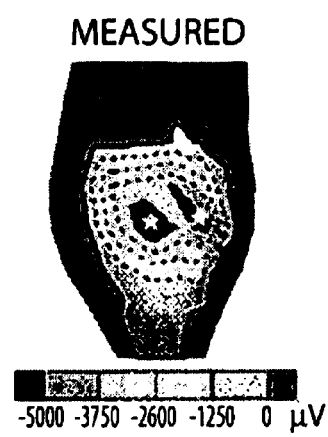
Figures 3, 20A:
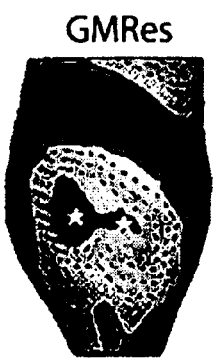
Figures 4, 20A:

FIG. 18 presents one illustrative block diagram for the disclosed systems and methods that employs a GMRes module to compute epicardial surface electric potentials based on body surface electrical potential data and geometrical relationships between the body surface and the epicardial surface. As FIG. 18 indicates, body surface electric potential data 802 can be provided by a vest 12 or other body surface device for measuring electric potentials (e.g., ECG/EKG, etc.), where such data can be input to a signal processing module 804 to determine a vector of body surface electric potentials, $V_T$. Further, a geometry determining device 24 such as a CT scan, MRI, bi-plane or single plane x-ray fluoroscopy, and other known techniques, can provide body surface data (e.g., vest electrode positions, etc.) and epicardial geometry data 806 which can be processed by an image processing module 808 and/or boundary element method module 810 to produce a transfer matrix, A, representing the geometric relationships between the body surface and epicardial surface. The A matrix and $V_T$ data can be prepared 811 for input to a GMRes module 812. Another input to the GMRes module 812 can be a maximum number of iterations 814. As provided herein, the GMRes module 812 can be repeated for a number of iterations 814 that can be equal to the maximum number of iterations 814, whereupon residual error and Hessenberg matrix data can be provided for the various iterations, including for example, other data based on the condition of the Hessenberg matrix at an iteration. Based on whether the FIG. 18 embodiment employs an automatic and/or a manual computation 816 of a GMRes number of iterations for approximating the A matrix inverse, data from the GMRes module can be used to determine an approximation for the A matrix inverse, and accordingly, at least one vector of epicardial surface potentials, $V_E$, can be computed or otherwise determined.

Based on a system and method according to FIG. 18, if a manual computation of a number of iterations for approximating the A matrix inverse is selected 816, data from the GMRes module 812 corresponding to the number of iterations can be employed to compute an approximation of the A matrix inverse, whereupon epicardial surface potentials, $V_E$, can also be computed based on the approximation and the body surface electric potentials, $V_T$. Also, if an automatic number of iterations is selected or otherwise designated 816, an iteration module 818 can be employed to determine a number of iterations upon which an approximation of the A matrix inverse can be computed (i.e., based on corresponding data from the GMRes module 812), and epicardial surface potentials, $V_E$, can be computed based on the approximation and the body surface electric potentials, $V_T$.

As indicated by the illustrative iteration module 818, one or more techniques can be used to determine a number of iterations from which to base the approximation of the A matrix inverse, where such techniques were previously described herein. Such "automatic" determination can be based on the GMRes module data, where, as provided herein, a plot or other comparison of residual error and Hessenberg matrix condition can be computed to determine a corner of a condition L curve. One or more of the illustrated techniques 818 and other methods can be used and compared, for example, to provide an iteration number. Data associated with the iteration number (e.g., Hessenberg matrix, etc.) can be retrieved from the GMRes module 812 or other location to compute an approximation to the A matrix inverse.

Several experiments were conducted using isolated canine hearts in a human-shaped torso tank, where a Langendorff perfused dog heart was suspended in an approximate anatomic position in a human-shaped torso tank to facilitate simultaneous recording of body surface and epicardial potentials for single and dual pacing from various sites.

For the single pacing embodiment, body surface and epicardial potentials were simultaneously recorded during pacing from a single anterior epicardial site to provide a data set for simulating an arrhythmogenic ectopic focus and providing data for evaluating the aforementioned GMRes systems and methods for localizing initiation sites of arrhythmic activity and other comparatively highly localized electrophysiological events.

For the dual pacing embodiment, epicardial potentials were recorded for simultaneous pacing from pacing sites distanced by 2.5 centimeters. The recorded potentials were used to compute body surface potentials in a computer model of the human torso that included the thoracic inhomogeneities of lungs, muscle, bone, and fluid layers. The computed body surface potentials were used to reconstruct epicardial potentials in a homogeneous torso of the same geometry. The dual pacing data set allowed an evaluation of the reconstruction accuracy of GMRes while assuming a homogeneous torso (an approximation that greatly simplifies the clinical application of ECGI), and an evaluation of the accuracy and spatial resolution of GMRes in localizing two closely-spaced pacing sites.

Additionally, open chest canine experiments were performed by measuring epicardial potentials from hearts of open chest dogs (i.e., exposed by sternotomy) using a multi-electrode epicardial sock. The open chest data was used to compute body surface potentials in a homogeneous or inhomogeneous computer model of the human torso. Measurement noise (e.g., 50 $\mu V$ peak-to-peak, Gaussian) and geometrical errors (e.g., 1 mm, Gaussian) were added to the body surface potentials and electrode positions, respectively, to simulate experimental or clinical measurements. These "contaminated" body surface potentials were then used to reconstruct epicardial potentials using the ECGI methodology.

Epicardial potentials during right atrial pacing (i.e., simulating normal sinus rhythm) were recorded from a 490-electrode sock. A region of infarcted tissue was created by the ligation of the left anterior descending coronary artery (LAD) and ethanol injection. This data set allowed an evaluation of the GMRes methods and systems to reconstruct abnormal electrophysiological properties of an infarct substrate.

Infarction was produced in a canine heart through ligation of the LAD. After four days of infarct formation in a closed chest, the chest was opened again and a 490-electrode sock pulled over the heart to record potentials. Monomorphic Ventricular Tachycardia (VT) due to double-loop epicardial reentry was induced through programmed stimulation and recorded. This data set was used to evaluate the GMRes methods and systems for reconstructing the reentry pathway and its various electrophysiological components.

Abnormal and heterogeneous repolarization is understood to be an underlying mechanism of many arrhythmias. Localized epicardial cooling was applied to prolong action potential duration in a region of the LV and consequently increase dispersion of repolarization. Epicardial potentials were recorded during RA pacing and QRST integral maps were computed to reflect local repolarization properties.

For the data sets presented herein, epicardial potentials were reconstructed using the GMRes method and the results were validated by direct comparison to measured epicardial potentials, which served as the gold standard. A zero initial value was used as a starting point for the GMRes iterations. The GMRes results were also compared with corresponding Tikhonov reconstructions. A hybrid method (Tik-GMRes method) was also developed and evaluated. In the hybrid method, GMRes solutions were computed with the Tikhonov solution (rather than zero) as the starting point for the iterative scheme.

Epicardial potential maps were reconstructed which depict the spatial distributions of potentials on an epicardial envelope of the heart. Although an epicardial potential map depicts one instant of time, epicardial potential maps were computed at intervals of one millisecond during an entire cardiac cycle. Electrograms were also reconstructed depicting the variation of potential with respect to time at a single point on the epicardium. The reconstructed electrograms were generally computed at approximately two-hundred to five-hundred sites or points around the epicardial envelope. Further, isochrone maps were reconstructed which depict the sequence of epicardial activation based on local activation time taken as the point of maximum negative derivative (−dV/dtmax) of each electrogram.

Results were based on visual comparison and, when possible, included statistical measures in the form of relative errors and correlation coefficients.

FIG. 19 shows epicardial potential maps for pacing from a single anterior ventricular site (indicated by asterisk), 25 milliseconds after a pacing stimulus. FIG. 19a presents directly measured epicardial potentials, with the corresponding GMRes and Tikhonov reconstructions shown in FIGS. 19b and 19c, respectively. The measured potentials display a central negative region containing a minimum at the pacing site (asterisk), flanked by two positive regions containing local maxima (+). FIG. 19D is adapted from Oster et al. (Oster H S, Taccardi B, Lux R L, Ershler P R, Rudy Y., "Noninvasive electrocardiographic imaging: reconstruction of epicardial potentials, electrograms, and isochrones and localization of single and multiple electrocardiac events," Circulation. 1997;96:1012–1024.) which shows an equivalent dipole source and theoretical potential pattern associated with single-site pacing. The illustrated pacing site is surrounded by a negative region which contains two potential minima (−). Two corresponding potential maxima (+) are present in the flanking positive region. The entire pattern is oriented along the axis of myocardial fibers (background lines) in this region. The reconstructed GMRes and Tikhonov maps (FIGS. 19b and 19c) capture the two minima in the central negative region. Note that the measured map, FIG. 19a, shows only one central minimum because of limited spatial resolution (insufficient density of measuring electrodes). The GMRes reconstruction is comparable in accuracy to the Tikhonov reconstruction, with both locating the pacing site to within three millimeters of the actual position, while both correctly reproduce the progression of potential patterns during the entire paced beat (only 25 milliseconds is shown). Similar accuracy was obtained for potential maps generated by left-lateral and postero-lateral pacing (not shown).

FIG. 20 shows epicardial potentials generated by simultaneous pacing from two closely spaced sites (e.g., 2.5 cm apart), indicated by asterisks. FIG. 20a shows potential maps during activation, or 25 ms after the pacing stimulus. Body surface potential maps (BSPM) shown in FIG. 20a(1) were the input data for the noninvasive GMRes and Tikhonov reconstructions. FIG. 20a(2) shows measured epicardial potentials with two potential minima at each of the two pacing sites. It is noted that the corresponding BSPM shows one minimum without an indication of dual pacing. From the smoothed BSPM data, the GMRes method provided reconstruction of two pacing sites with reasonable localization accuracy, with the left minimum within four millimeters, and right minimum within six millimeters of the corresponding pacing sites (FIG. 20a(3)). The Tikhonov method (FIG. 20a(4)) allows reconstruction of one elongated minimum, which suggests more than one pacing site, yet this method fails to capture or otherwise detect two distinct minima. It is noted that a smoothing property of such constrained regularization can cause a loss of spatial resolution.

FIG. 20b shows potential maps during repolarization, or 90 milliseconds after the pacing stimulus. The repolarization pattern is similar to the activation pattern, except that the polarity is reversed. Accordingly, two maxima, indicated by +, correspond to the minima at the pacing site locations for the activation pattern. Referring to FIG. 20b(1), one maximum is present in the BSPM, while in FIG. 20b(3), the GMRes reconstructed repolarization pattern includes two maxima. The Tikhonov method reconstruction, shown in FIG. 20b(4), includes one elongated maximum.

Based on FIG. 20, in certain embodiments, a method and system that employs GMRes can resolve multiple electrophysiological events (e.g., initial activation sites) with higher spatial resolution than a constraint-based Tikhonov approach.

Figure 21A:
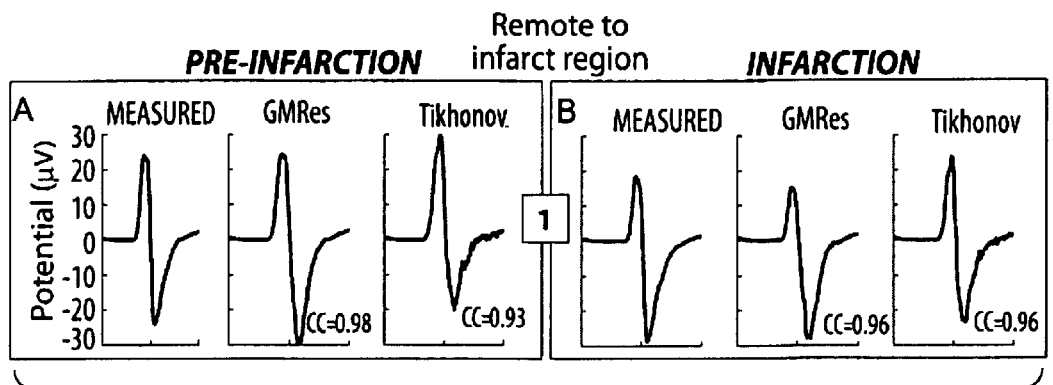
FIGS. 21a, 21b, and 21c present electrograms from a first site on the right ventricle, and second and third sites in the left ventricle, respectively.
Figure 21B:
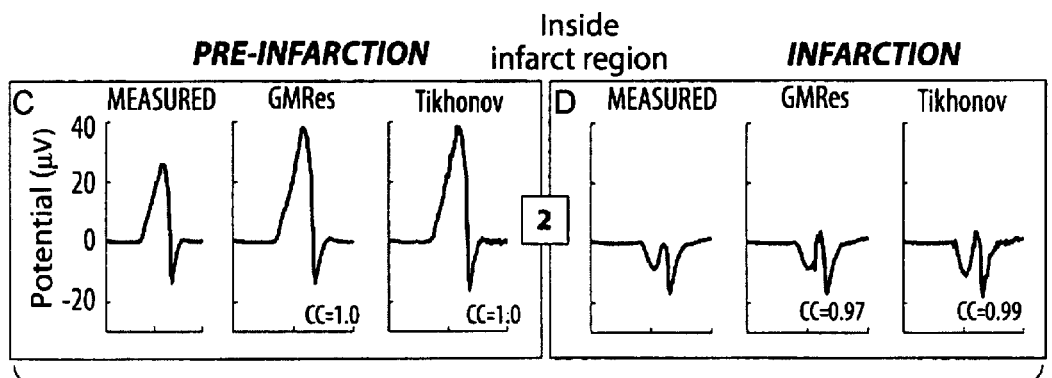
Figure 21C:
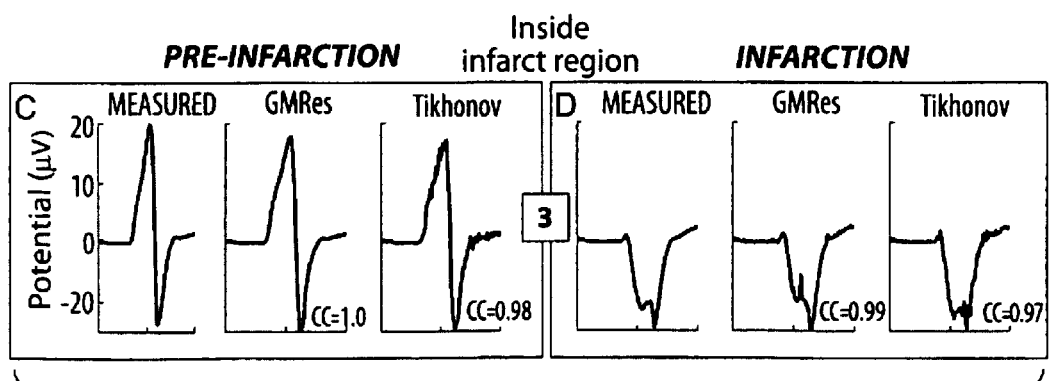
Figure 22A:
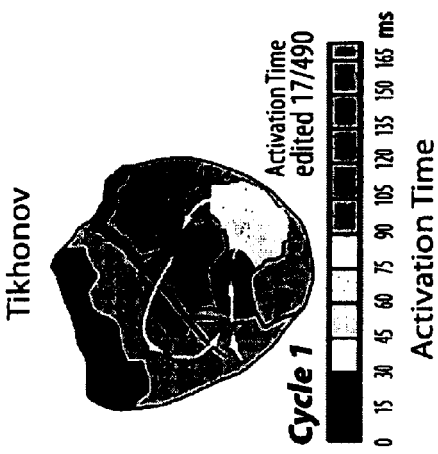
FIGS. 22a and 22b show isochrones constructed from measured electrograms.
Figure 22E:
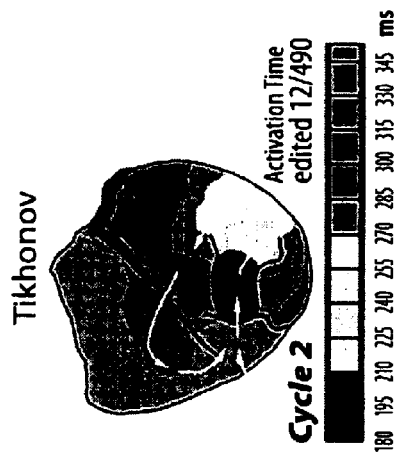
FIGS. 22e and 22f show isochrones based on Tikhonov reconstruction.
Figure 22C:
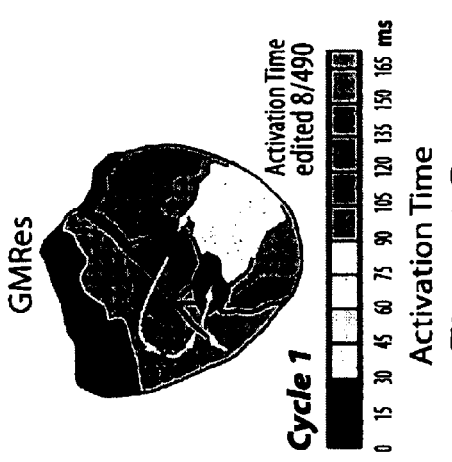
FIGS. 22c and 22d show isochrones based on GMRes reconstruction.
Figure 22D:
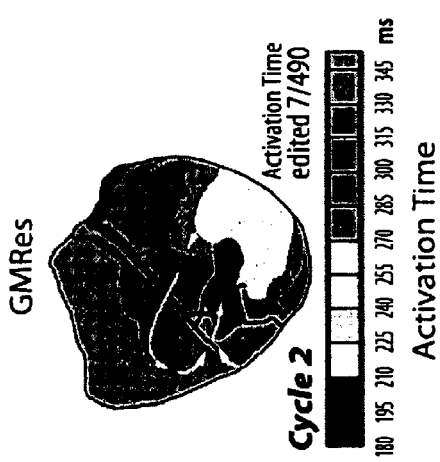
Figure 22B:
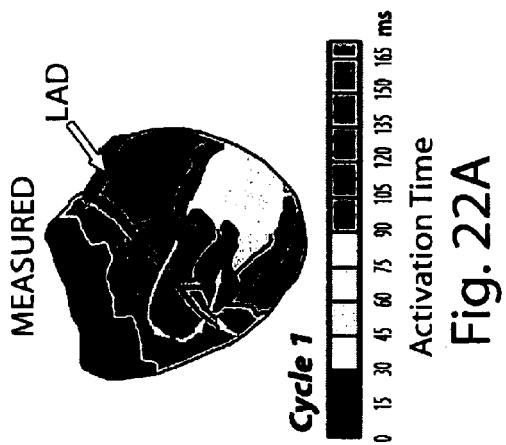
Figure 22F:

FIG. 21 shows epicardial electrograms pre-infarction and post-infarction. FIG. 21a shows electrograms from a first site located on the right ventricle, remote to the LV infarct location. Panel A shows electrograms from the control heart (pre-infarction), with directly measured electrograms and corresponding GMRes and Tikhonov (Tik) reconstructions. Electrograms from the infarcted heart from the same location are shown in panel B. The measured electrograms pre-infarction and post-infarction show normal RS morphology with a sharp intrinsic deflection indicating local activation (i.e., electrograms at this location are not affected by the remote infarct and maintain their pre-infarction morphology). Both GMRes and Tikhonov reconstructions show similarity to the measured electrograms. FIGS. 21b and 21c show electrograms from second and third sites, respectively, in the LV inside the infarct region. Panel C shows pre-infarction electrograms and panel D post-infarction electrograms. Pre-infarction electrograms from the second and third sites show typical RS morphology similar to the first site; however, the infarct produces a change in their morphology from RS waves (panel C) to negative slow Q waves (panel D). The Q waves contain superimposed sharp small deflections that likely indicate local activation of islands of surviving myocardium within the infarct. The GMRes reconstructions and Tikhonov reconstructions show similarity to the directly measured electrograms and capture the infarction-induced changes, including the smaller deflections generated by surviving myocardium. The Tikhonov electrograms are "jagged" in appearance due to the variation in regularization parameter from time-frame to time-frame. The corresponding GMRes electrograms are smoother, without sacrificing detail in the measured electrograms.

FIG. 22 shows isochrone maps for two cycles of monomorphic ventricular tachycardia (VT). FIGS. 22a and 22b show isochrones constructed from activation times determined from directly measured electrograms. The VT is caused by double loop reentry (black arrows) with a central common pathway in the infarct region between two lines of conduction block (thick black lines). FIGS. 22c, 22d and FIGS. 22e, 22f show corresponding GMRes and Tikhonov reconstructions, respectively. The reconstructions capture the features of the reentrant circuit, showing correlation with the measured isochrones for the two displayed cycles. For similar accuracy, however, the GMRes reconstruction included about half as much manual editing of activation times as the corresponding Tikhonov reconstruction. Actual numbers of edited activation times are shown on the bottom right side of each reconstructed map.

Figure 23:
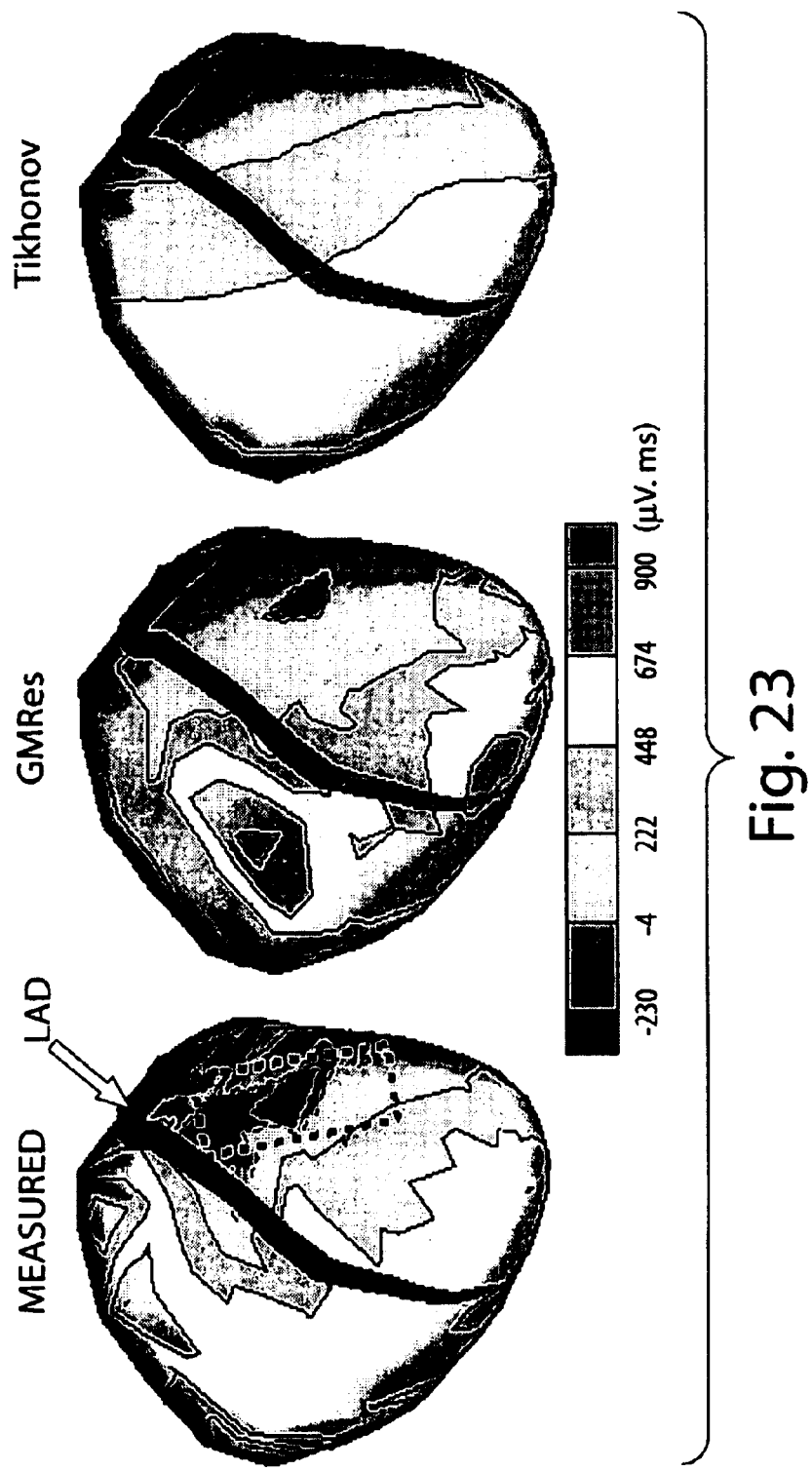
FIG. 23 presents directly measured, GMRes reconstructed, and Tikhonov reconstructed QRST integral maps during local LV cooling; and, FIGS. 24a and 24b show a measured potential map and a corresponding Tikhonov-GMRes hybrid reconstruction, respectively.

FIG. 23 presents directly measured, GMRes reconstructed, and Tikhonov reconstructed epicardial QRST integral maps during local LV cooling. The cooling probe position is shown by the dotted rectangle of the measured map. The measured QRST integral map shows lower QRST amplitudes in the region of cooling with a localized minimum directly under the cooling probe. Although the GMRes and Tikhonov reconstructions show the cooling-induced reduction in QRST integral values similar to the measured map, the GMRes reconstructs the localized minimum under the cooling probe, while the Tikhonov does not. The Tikhonov reconstruction is smoothed, resulting in loss of spatial resolution and under-representation of local repolarization heterogeneities.

Figure 24A:
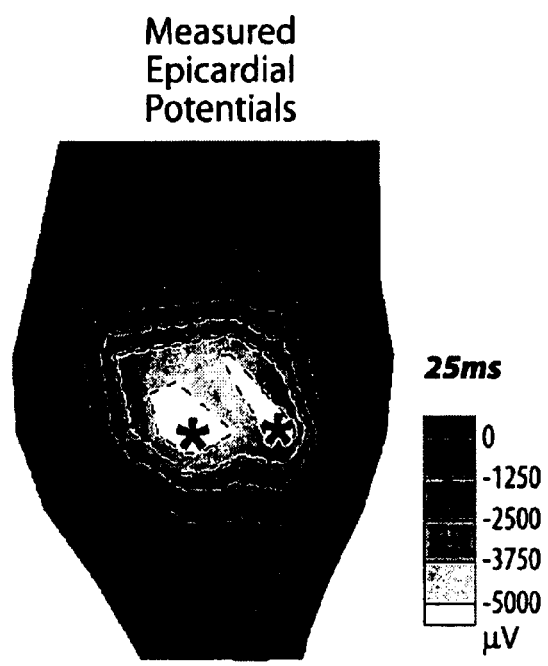
Figure 24B:
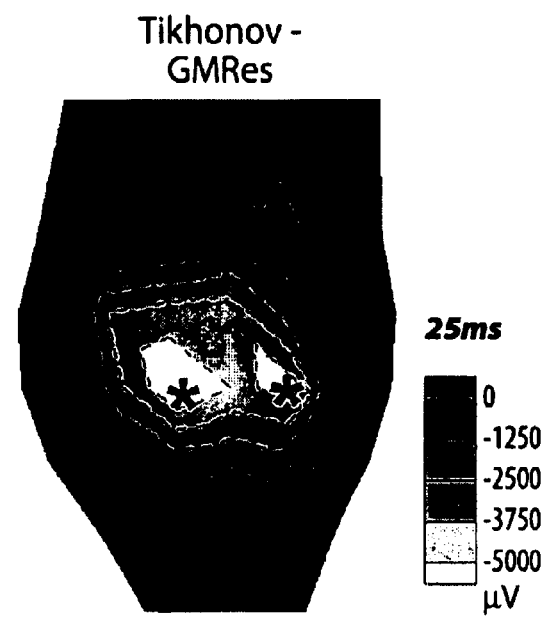

FIG. 24 shows reconstructions using the Tikhonov-GMRes hybrid method applied to the simultaneous dual pacing data of FIG. 20. FIG. 24a shows a measured potential map for a time-frame of 25 milliseconds after the pacing stimulus, while FIG. 24b provides a corresponding Tikhonov-GMRes hybrid reconstruction. FIG. 24b indicates a closer correlation with the pattern of the measured map when compared to the independent application of the GMRes or Tikhonov methods (see FIG. 20). The hybrid method also more accurately locates (e.g., within 1 millimeter) the pacing sites when compared to the independent application of GMRes or Tikhonov methods (see again, FIG. 20).

The sensitivity of the GMRes method to potential noise and geometry errors was also evaluated using the data set of FIG. 19. Various combinations of potential noise (either 50 microvolt or 100 microvolt, Gaussian) and geometrical errors in torso-electrode positions (either one, two, or three millimeter, Gaussian) were added to the input data. The quality of the GMRes solution was comparable to the solution obtained with original data without the added noise.

Further, the hybrid method, which included starting with the Tikhonov solution rather than an initial value of "zero" for GMRes, improved the patterns and localization accuracy of the reconstruction of two pacing sites (FIG. 24). For other data sets, some improvement in accuracy was observed when using the hybrid method.

What has thus been described are methods and systems for computing epicardial surface electric potentials based on measured body surface electric potentials, where the methods and systems include representing at least one geometric relationship between at least one body surface electric potential measuring system and the epicardial surface as a multidimensional matrix, estimating an inverse of the multidimensional matrix based on a Generalized Minimum Residual (GMRes) method, and, based on the inverse matrix and the measured body surface potentials, determining the epicardial surface electric potentials. Also disclosed is a method for determining the geometric relationship by employing 2D image data to reconstruct a 3D surface using epipolar geometry.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) is preferably implemented using one or more high level procedural or object-oriented programming languages to communicate with a computer system; however, the program(s) can be implemented in assembly or machine language, if desired. The language can be compiled or interpreted.

As provided herein, the processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a processor" or "the processor" can be understood to include one or more processors that can communicate in a stand-alone and/or a distributed environment(s), and can thus can be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application.

Although the methods and systems have been described relative to a specific embodiment thereof, they are not so limited. Obviously many modifications and variations may become apparent in light of the above teachings. For example, although the methods and system can be applied to cardiac applications, those of ordinary skill will recognize that other anatomical parts can be imaged accordingly.

Further, although the reconstructed data was employed to generate images, electrograms, and isochrones, other data representations can be employed. Although the methods and systems refer to image data received from bi-plane fluoroscopy, multi-planar fluoroscopy may also be employed.

Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A method for computing epicardial surface electric potentials based on measured body surface electric potentials, the method comprising:
    generating a multidimensional matrix, the matrix representing at least one geometric relationship between at least one body surface electric potential measuring system and the epicardial surface, the multidimensional matrix being based on:
        at least one first two-dimensional (2D) image of the epicardium using a first imaging device,
        at least one second 2D image of the epicardium using a second imaging device,
        a first projection matrix associated with the first imaging device,
        a second projection matrix associated with the second imaging device,
        a computed contour of the outer surface of the heart formed from contours identified in the at least one first 2D image and the at least one second 2D image,
        a computed contour of the electric potential measuring system, and,
        a boundary element method based on the computed contour of the outer surface of the heart and the computed contour of the electric potential measuring system,
    using a Generalized Minimum Residual (GMRes) method to estimate an inverse of the multidimensional matrix, and,
    based on the inverse matrix and the measured body surface potentials, determining the epicardial surface electric potentials.

2. A method according to claim 1, where representing includes measuring the position of the at least one body surface electric potential measuring system.

3. A method according to claim 1, where using a GMRes method includes determining a number of iterations for the GMRes method.

4. A method according to claim 3, where using a GMRes method includes providing a maximum number of iterations for the GMRes method, and based on the data from the maximum number of iterations, determining a number of iterations for the GMRes method.

5. A method according to claim 3, where determining a number of iterations includes comparing residual error to a Hessenberg matrix condition, and computing at least one of a corner of a condition L curve and a maximum curvature of a condition L curve.

6. A method according to claim 3, where determining a number of iterations includes determining a number of iterations based on at least one of: a corner of a condition L curve, a corner of an L curve, an increase in spatial frequency of a reconstructed potential map, and an increase in amplitude of a solution norm.

7. A method according to claim 1, where using a GMRes method includes providing an initial condition of zero.

8. A method according to claim 1, where using a GMRes method includes providing an initial condition based on a Tikhonov regularization of the multidimensional matrix.

* * * * *